United States Patent [19]

Grant et al.

[11] Patent Number: 5,484,940
[45] Date of Patent: Jan. 16, 1996

[54] SUBSTITUTED 3-INDOLYL-5-PYRAZOLONE COMPOUNDS

[76] Inventors: Francine S. Grant; Lawrence Y. Fang; Varghese John; Eugene D. Thorsett, all of 800 Gateway Blvd., South San Francisco, Calif. 94080

[21] Appl. No.: 345,973

[22] Filed: Nov. 28, 1994

[51] Int. Cl.$^6$ .................. C07D 403/08; C07D 403/14
[52] U.S. Cl. .................. 548/364.7; 544/238; 544/284
[58] Field of Search .................. 548/364.7; 544/238, 544/284

[56] References Cited

U.S. PATENT DOCUMENTS

| | | | |
|---|---|---|---|
| 3,161,654 | 12/1964 | Shen | 260/319 |
| 3,190,889 | 6/1965 | Shen | 260/319 |
| 3,201,414 | 8/1965 | Shen | 260/319 |
| 3,242,162 | 3/1966 | Sarett | 260/211 |
| 4,666,829 | 5/1987 | Glenner | 435/6 |

FOREIGN PATENT DOCUMENTS

WO94/10569  5/1994  WIPO .

OTHER PUBLICATIONS

Baran, et al., "The Cyclooxgenase and Lipoxygenase Inhibitor BW755C Protects Rats Against Kainic Acid–Induced Seizures and Neurotoxicity," *Brain Research* 646:201–206 (1994).
Citron, et al., *Nature* 360:672–674 (1992).
Brewer, et al., *J. Neurosci. Res.* 35(5):567–576 (1993).
Coleman, "Phenylhydrazine," *Organic Synthesis* Coll. vol. 1, pp. 442–445 (1953).
Egan, et al., "Inhibition of Mammalian 5–Lipoxygenase by Aromatic Disulfides," *J. Biol. Chem.* 260:11554–11559 (1985).
Ghali, et al., "A High–Yielding Synthesis of Monoalkylhydrazines," *J. Org. Chem.* 46:5413–5414 (1981).
Hansen, et al., *J. Immun. Meth.* 119:203–210 (1989).
Ford–Hutchinson, et al., *Ann. Rev. Biochemistry* 63:383–417 (1994).
Mansour and Evans, "Decarboxylative Carbon Acylation of Malonates with Aminoacylimidazolides Mediated by Lewis Acids," *Synth. Commun.* 20(5):773–781 (1990).
Selkoe, "Amyloid Protein and Alzheimer's Disease," *Scientific American*, pp. 2–8, Nov., (1991).
Seubert et al., *Nature* 359:325–327 (1992).
Shimuzu, et al., "Enzyme with Dual Lipoxygenase Activities Catalyzes Leukotriene A4 Synthetase from Arachidonic Acid," *Proc. Natl. Acad. Sci. USA* 81:689–693 (1984).
Wierenga and Skulnick, "General Efficient, One–Step Synthesis of β–Keto Esters," *J. Org. Chem* 44:310–311 (1979).
Yamamoto, et al., "I–Acylindoles. IV. Novel Syntheses of 1–Benzoylindole–3—aliphatic Acids," *Chem. Pharm. Bull.* 16(4):647–653 (1968).

*Primary Examiner*—Jacqueline Haley

[57] ABSTRACT

This invention is directed to novel substituted 3-indolyl-5-pyrazolone compounds as well as intermediates useful in the preparation of such substituted 3-indolyl-5-pyrazolone compounds.

11 Claims, No Drawings

SUBSTITUTED 3-INDOLYL-5-PYRAZOLONE COMPOUNDS

BACKGROUND OF THE INVENTION

1. Field of the Invention

This invention is directed to novel substituted 3-indolyl-5-pyrazolone compounds as well as intermediates useful in the preparation of such substituted 3-indolyl-5-pyrazolone compounds. This invention is also directed to methods for the use of such substituted 3-indolyl-5-pyrazolone compounds.

2. References

The following publications and patent application are cited in this application as superscript numbers at the relevant portion of the application:

[1] Schenk, et al., International Patent Application Publication No. WO 94/10569, "*Methods and Compositions for the Detection of Soluble β-Amyloid Peptide*", published 11 May 1994

[2] Selkoe, Scientific American, "*Amyloid Protein and Alzheimer's Disease*", pp. 2–8, November, 1991

[3] Mansour and Evans, Synth. Commun., "*Decarboxylative Carbon Acylation of Malonates with Aminoacylimidazolides Mediated by Lewis Acids*", 20(5):773–781 (1990)

[4] Wierenga and Skulnick, J. Org. Chem., "*General, Efficient, One-Step Synthesis of β-Keto Esters*", 44:310–311 (1979)

[5] Ghali, et al., J. Org. Chem., "A High-Yielding Synthesis of Monoalkylhydrazines", 46:5413–5414 (1981)

[6] Coleman, Organic Synthesis, "*Phenylhydrazine*", Coll. Vol. 1, pp. 442–445

[7] Yamamoto, et al., Chem. Pharm. Bull., "*1-Acylindoles. IV. Novel Syntheses of 1-Benzoylindole-3-aliphatic Acids*", 16(4):647–653 (1968)

[8] Shen, U.S. Pat. No. 3,190,889, "*1-Substituted-3-Indolyl Aliphatic Acids*", issued Jun. 22, 1965

[9] Sarett, et al., U.S. Pat. No. 3,242,162, "*Indolyl Aliphatic Acids*", issued Mar. 22, 1966

[10] Shen, U.S. Pat. No. 3,201,414, "*New 1-Heteroacyl-3-Indolyl Aliphatic Acids*", issued Aug. 17, 1965

[11] Shen, U.S. Pat. No. 3,161,654, "*60 -(1-Aroyl-3-Indolyl)Alkanoic Acids*", issued Dec. 15, 1964

[12] Glenner, et al., "*Polypeptide Marker for Alzheimer' Disease and its Use ofr Diagnosis*", U.S. Pat. No. 4,666,829, issued May 19, 1987

[13] Wiley and Wiley, The Chemistry of Heterocyclic Compounds, Vol. 20, Interscience, New York, N.Y. (1964)

[14] Hutchinson, et al., Ann. Rev. Biochemistry, 63:383–417 (1994)

[15] Baran, et al., Brain Research, *The Cyclooxgenase and Lipoxygenase Inhibitor BW755C Protects Rats Against Kainic Acid-Induced Seizures and Neurotoxicity*", 646:201–206 (1994)

[16] Citron, et al., Nature, 360:672–674 (1992)

[17] Hansen, et al., J. Immun. Meth., 119:203–210 (1989)

[18] Shimuzu, et al., *Enzyme with Dual Lipoxygenase Activities Catalyzes Leukotriene A4 Synthetase from Arachidonic Acid*, Proc. Natl. Acad. Sci. USA, 81:689–693 (1984)

[19] Egan, et al., *Inhibition of Mammalian 5-Lipoxygenase by Aromatic Disulfides*, J. Biol. Chem., 260:11554–11559 (1985)

[20] Brewer, et al., J. Neurosci. Res., 35(5)567–576 (1993)

[21] Seubert, et al., Nature, 359:325–327 (1992)

All of the above publications, patent applications and patents are herein incorporated by reference in their entirety to the same extent as if each individual publication, patent application or patent was specifically and individually indicated to be incorporated by reference in its entirety.

SUMMARY OF THE INVENTION

This invention is directed to novel 3-indolyl-5-substituted pyrazolone compounds having a variety of uses including use as additives in plastic compositions and as pharmaceuticals. In particular, the compounds disclosed herein can absorb ultraviolet (UV) light and, accordingly, are useful as additives in plastic compositions and the like where absorption of UV light is an important requirement of the composition.

Additionally, the compounds described herein are useful in pharmaceutical compositions. For example, the compounds described herein possess anti-inflammatory properties whereas some of the compounds also are able to inhibit both in vivo and in vitro the generation of β-amyloid peptide in, for example, a cultured cell medium as well as inhibiting the toxicity of the β-amyloid peptide toward human neuronal cells. In turn, in vivo generation of β-amyloid peptide is known to be associated with the pathogenesis of Alzheimer's Disease (AD)[1-2] wherein such pathogenesis is also associated with toxicity of the β-amyloid peptide toward human neuronal cells. Accordingly, those compounds which inhibit β-amyloid generation and/or reduce toxicity of the β-amyloid peptide toward human neuronal cells are useful both prophylactically and therapeutically in the prevention and treatment of AD.

Accordingly, in one of its composition aspects, this invention is directed to a compound of formula I:

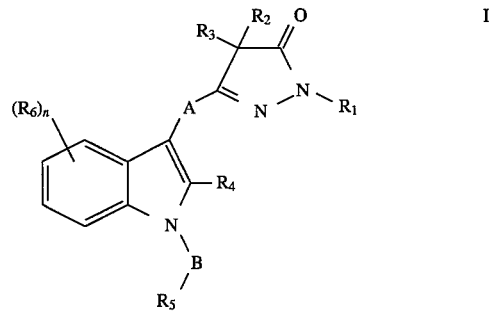

wherein $R_1$ is selected from the group consisting of
hydrogen,
alkyl of from 1 to 10 carbon atoms optionally substituted with 1 to 4 substituents selected from the group consisting of halo, —$NR_7R_8$, —$NR_7C(O)R_8$ where $R_7$ and $R_8$ are independently selected from the group consisting of hydrogen and alkyl of from 1 to 10 carbon atoms, aryl of from 6 to 10 carbon atoms, aryl of from 6 to 10 carbon atoms substituted with from 1 to 3 substituents selected from the group consisting of halo, cyano, nitro, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms, cycloalkyl of from 3 to 8 carbon atoms, aryl of from 6 to 10 carbon atoms optionally substituted with from 1 to 3 substituents selected from the group consisting of halo, cyano, nitro, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms, and heterocycles having from 2 to 8 carbon atoms and from 1 to 3 heteroatoms selected from the group consisting of oxygen, sulfur and nitrogen;

$R_2$ and $R_3$ are independently selected from the group consisting of hydrogen, alkyl of from 1 to 10 carbon atoms, and where $R_2$ and $R_3$ together define a substituent of the formula $=CR_{13}R_{14}$ where $R_{13}$ and $R_{14}$ are independently selected from the group consisting of hydrogen, alkyl of from 1 to 10 carbon atoms and phenyl;

$R_4$ is selected from the group consisting of hydrogen and alkyl of from 1 to 10 carbon atoms;

$R_5$ is selected from the group consisting of hydrogen, alkyl of from 1 to 10 carbon atoms optionally substituted with from 1 to 4 substituents selected from the group consisting of halo, $-NR_7R_8$, $-NR_7C(O)R_8$ where $R_7$ and $R_8$ are independently selected from the group consisting of hydrogen and alkyl of from 1 to 10 carbon atoms, aryl of from 6 to 10 carbon atoms optionally substituted with from 1 to 3 substituents selected from the group consisting of halo, nitro, cyano, alkyl of from 1 to 10 carbon atoms, haloalkyl of from 1 to 10 carbon atoms and at least 1 halo substituent, alkoxy of from 1 to 10 carbon atoms, $-NR_7R_8$, $-NR_7C(O)R_8$ where $R_7$ and $R_8$ are independently selected from the group consisting of hydrogen and alkyl of from 1 to 10 carbon atoms, each, $R_6$ is independently selected from the group consisting of halo, nitro, alkyl of from 1 to 10 carbon atoms, haloalkyl of from 1 to 10 carbon atoms and at least 1 halo substituent, alkoxy of from 1 to 10 carbon atoms, $-NR_7R_8$, $-NR_7C(O)R_8$ where $R_7$ and $R_8$ are independently selected from the group consisting of hydrogen and alkyl of from 1 to 10 carbon atoms;

n is an integer of from 0 to 3;

A is selected from the group consisting of $X-R_9-$ where X is selected from the group consisting of a bond, O and $S(O)_p$ where p is an integer of from 0 to 2 and $R_9$ is an alkylene group of from 1 to 6 carbon atoms; and B is selected from the group consisting of a bond, an alkylene group of from 1 to 6 carbon atoms, $-R_{10}-Y-$ where $R_{10}$ is selected from the group consisting of a bond and an alkylene group of 1 to 4 carbon atoms and Y is selected from the group consisting of $-C(O)-$ and $-S(O)_q-$ where q is an integer of from 0 to 2, and $-C(O)Z-$ where Z is selected from the group consisting of O, S, and $-NR_{11}$ where $R_{11}$ is hydrogen or alkyl of from 1 to 10 carbon atoms;

with the proviso that when $R_2$ and/or $R_3$ is hydrogen, the compounds of formula I above can exist in the tautomeric form illustrated in formula II below:

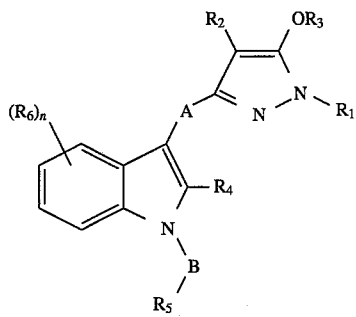

II

As it relates to the R substituents, preferred compounds of formula I and formula II of this invention include those where both $R_2$ and $R_3$ are hydrogen;

where $R_1$ is selected from the group consisting of alkyl of from 1 to 10 carbon atoms, aryl of from 6 to 10 carbon atoms optionally having from 1 to 2 substituents selected from the group consisting of fluoro, chloro, bromo, nitro, alkyl of from 1 to 3 carbon atoms, trihalomethyl, alkoxy of from 1 to 3 carbon atoms, $-NR_7R_8$, $-NR_7C(O)R_8$ where $R_7$ and $R_8$ are independently selected from the group consisting of hydrogen and alkyl of from 1 to 3 carbon atoms;

where $R_4$ is selected from the group consisting of hydrogen and methyl;

where $R_5$ is selected from the group consisting of aryl of from 6 to 10 carbon atoms optionally substituted with from 1 to 4 substituents selected from the group consisting of halo, cyano, nitro, alkyl of from 1 to carbon atoms, haloalkyl of from 1 to 10 carbon atoms and at least 1 halo substituent, alkoxy of from 1 to 10 carbon atoms, $-NR_7R_8$, $-NR_7C(O)R_8$ where $R_7$ and $R_8$ are independently selected from the group consisting of hydrogen and alkyl of from 1 to 10 carbon atoms; and where $R_6$ is selected from the group consisting of alkyl of from 1 to 10 carbon atoms, alkoxy of from 1 to 10 carbon atoms, chloro, and n is an integer equal to 1.

It is understood, however, that the preferred R substituents recited above can be employed by themselves in formula I and formula II and/or can be employed in combination with other preferred R substituents. For example, one preferred group of compounds of formula I and II above include those compounds where $R_4$ is hydrogen or methyl and another preferred group of compounds of formula I and II above include those compounds where $R_2$ and $R_3$ are hydrogen and $R_4$ is hydrogen or methyl.

Additional preferred compounds of formula I and formula II above include those compounds where the A substituent is an alkylene group of from 1 to about 6 carbon atoms.

Still additional preferred compounds of formula I and formula II above include those compounds where the B substituent is selected from the group consisting of a bond or an alkylene group of from 1 to 4 carbon atoms and $-C(O)-$.

Representative compounds included within the scope of formula I and II of this invention include those set forth below:

3-[1-(4-chlorobenzoyl)-5-methoxy-2-methyl-3-indolylmethyl]-1-phenyl-5-pyrazolone 3-[1-(4-chlorobenzoyl)-5-methoxy-2-methyl-3-indolylmethyl]-1-cyclohexyl-5-pyrazolone 3-[1-(4-chlorobenzoyl)-5-methoxy-2-methyl-3-indolylmethyl]-1-cyclobutyl-5-pyrazolone 3-[1-(4-chlorobenzoyl)-5-methoxy-2-methyl-3-indolylmethyl]-1-cyclopentyl-5-pyrazolone 3-[1-(4-chlorobenzoyl)-5-methoxy-2-methyl-3-indolylmethyl]-1-cycloheptyl-5-pyrazolone 3-[1-(4-chlorobenzoyl)-5-methoxy-2-methyl-3-indolylmethyl]-1-benzyl-5-pyrazolone 3-[1-(4-chlorobenzoyl)-5-methoxy-2-methyl-3-indolylmethyl]-1-t-butyl-5-pyrazolone 3-[1-(4-chlorobenzoyl)-5-methoxy-2-methyl-3-indolylmethyl]-5-pyrazolone 3-[1-(4-chlorobenzoyl)-5-methoxy-2-methyl-3-indolylmethyl]-1-(4-heptyl)- 5-pyrazolone 3-(5-methoxy-2-methyl-3-indolylmethyl)-1-cyclohexyl-5-pyrazolone 3-[1-(4-chlorobenzoyl)-3-indolylmethyl]-1-cyclohexyl-5-pyrazolone 3-(1-benzyl-5-methoxy-2-methyl-3-indolylmethyl)-1-cyclohexyl-5-pyrazolone 3-[1-(4-chlorobenzoyl)-5-methoxy-2-methyl-3-indolyl-ethyl]-1-cyclohexyl-5-pyrazolone
3-[1-(4-chlorobenzoyl)-2-methyl-3-indolylmethyl]-1-cyclohexyl-5-pyrazolone
3-[1-(4-chlorobenzoyl)-5-methoxy-2-methyl-3-indolylmethyl]-1-(4-methoxyphenyl)-5-pyrazolone
3-[1-(4-chlorobenzoyl)-5-methoxy-2-methyl-3-indolylmethyl]-1-(3-methoxyphenyl)-5-pyrazolone
3-[1-(4-chlorobenzoyl)-5-methoxy-2-methyl-3-indolylmethyl]-1-( 3-trifluoromethylphenyl)-5-pyrazolone
3-[1-(4-chlorobenzoyl)-5-methoxy-2-methyl-3-indolylmethyl]-1-(3-chlorophenyl)- 5-pyrazolone
3-[1-(4-chlorobenzoyl)-5-methoxy-2-methyl-3-indolylmethyl]-1-(3,5-dichlorophenyl)- 5-pyrazolone
3-[1-(4-chlorobenzoyl)-5-methoxy-2-methyl-3-indolylmethyl]-1-(3-bromophenyl)- 5-pyrazolone
3-[1-(4-chlorobenzoyl)-5-methoxy-2-methyl-3-indolylmethyl]-1-(3,5-dimethylphenyl)- 5-pyrazolone
3-[1-(4-chlorobenzoyl)-5-methoxy-2-methyl-3-indolylmethyl]-1-(3-nitrophenyl)- 5-pyrazolone
3-[1-(4-chlorobenzoyl)-5-methoxy-2-methyl-3-indolylmethyl]-1-(3-methylphenyl)- 5-pyrazolone
3-[1-(4-chlorobenzoyl)-5-methoxy-2-methyl-3-indolylmethyl]-1-(3-fluorophenyl)- 5-pyrazolone
3-[1-(4-chlorobenzoyl)-5-methoxy-2-methyl-3-indolylmethyl]-1-(3,4-dichlorophenyl)- 5-pyrazolone
3-[1-(4-chlorobenzoyl)-5-methoxy-2-methyl-3-indolylmethyl]-1-(4-methylphenyl)- 5-pyrazolone
3-[1-(4-chlorobenzoyl)-5-methoxy-2-methyl-3-indolylmethyl]-1-(3-methyl- 6-pyridazinyl)-5-pyrazolone
3-[1-(4-chlorobenzoyl)-5-methoxy-2-methyl-3-indolylmethyl]-1-(2-quinoxalinyl)- 5-pyrazolone
3-[1-(4-chlorobenzoyl)-5-methoxy-2-methyl-3-indolylmethyl]-1-( 4-trifluoromethylphenyl)- 5-pyrazolone
3-[1-(3,4-dichlorobenzoyl)-5-methoxy-2-methyl-3-indolyl-methyl]-1-cyclohexyl- 5-pyrazolone
3-[1-(4-chlorobenzoyl)-5-methoxy-2-methyl-3-indolylmethyl]-1-(3-aminophenyl)- 5-pyrazolone
3-[1-(4-chlorobenzoyl)-5-methoxy-2-methyl-3-indolylmethyl]-1-(3-acetamidophenyl)- 5-pyrazolone
3-[1-(4-dichlorobenzoyl)-5-methoxy-2-methyl-3-indolylmethyl]-1-cyclohexyl-4-methyl- 5-pyrazolone
3-[1-(4-dichlorobenzoyl)-5-methoxy-2-methyl-3-indolylmethyl]-1-cyclohexyl- 4,4-dimethyl-5-pyrazolone
3-[1-(4-dichlorobenzoyl)-5-methoxy-2-methyl-3-indolylmethyl]-1-cyclohexyl- 4-benzylidene-5-pyrazolone
3-[1-(4-chlorobenzoyl)-5-methoxy-2-methyl-3-indolylmethyl]-1-methyl-5-pyrazolone
3-[1-(4-chlorobenzoyl)-5-methoxy-2-methyl-3-indolylmethyl]-1-(3,4-dimethylphenyl)- 5-pyrazolone
3-(3-indolylmethyl)-1-cyclohexyl-5-pyrazolone
3-(3-indolyl-n-propyl)-1-cyclohexyl-5-pyrazolone
3-[1-(4-chlorobenzoyl)-3-indolylmethyl]-5-pyrazolone
3-[1-(benzoyl)-5-methoxy-2-methyl-3-indolylmethyl]-1-(3-trifluoromethyl)- 5-pyrazolone
3-[1-(4-methoxybenzoyl)-5-methoxy-2-methyl-3-indolylmethyl]-1-(3-trifluoromethyl)- 5-pyrazolone
3-[1-(2-naphthoyl)-5-methoxy-2-methyl-3-indolylmethyl]-1-(3-trifluoromethyl)- 5-pyrazolone
3-[1-(4-cyanobenzoyl)-5-methoxy-2-methyl-3-indolylmethyl]-1-( 3-trifluoromethylphenyl)-5-pyrazolone
3-[1-benzyl-2-methyl-3-indolylmethyl]-1-cyclohexyl-5-pyrazolone
3-[1-phenyl-2-methyl-3-indolylmethyl]-1-cyclohexyl-5-pyrazolone
3-[3-indolylethyl]-1-cyclohexyl-5-pyrazolone In still another of its composition aspects, this invention is directed to a compound of formula III:

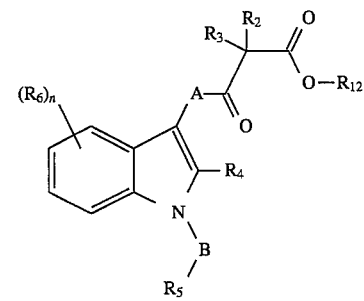

wherein
$R_2$ and $R_3$ are independently selected from the group consisting of hydrogen, alkyl of from 1 to 10 carbon atoms, and where $R_2$ and $R_3$ together define a substituent of the formula $=CR_{13}R_{14}$ where $R_{13}$ and $R_{14}$ are independently selected from the group consisting of hydrogen, alkyl of from 1 to 10 carbon atoms and phenyl;

$R_4$ is selected from the group consisting of hydrogen and alkyl of from 1 to 10 carbon atoms;

$R_5$ is selected from the group consisting of
hydrogen,
alkyl of from 1 to 10 carbon atoms optionally substituted with from 1 to 4 substituents selected from the group consisting of halo, —$NR_7R_8$, —$NR_7C(O)R_8$ where $R_7$ and $R_8$ are independently selected from the group consisting of hydrogen and alkyl of from 1 to 10 carbon atoms,
aryl of from 6 to 10 carbon atoms optionally substituted with from 1 to 3 substituents selected from the group consisting of halo, cyano, nitro, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms, each $R_6$ is independently selected from the group consisting of halo, nitro, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms;

n is an integer of from 0 to 3;

$R_{12}$ is alkyl of from 1 to 10 carbon atoms;

A is selected from the group consisting of X—$R_9$— where X is selected from the group consisting of a bond, O and $S(O)_p$ where p is an integer of from 0 to 2 and $R_9$ is an alkylene group of from 1 to 6 carbon atoms; and B is selected from the group consisting of a bond, an alkylene group of from 1 to 6 carbon atoms, —$R_{10}$—Y— where $R_{10}$ is selected from the group consisting of a bond and an alkylene group of 1 to 4 carbon atoms and Y is selected from the group consisting of —C(O)— and —$S(O)_q$— where q is an integer of from 0 to 2, and —C(O)Z— where Z is selected from the group consisting of O, S, and —$NR_{11}$ where $R_{11}$ is hydrogen or alkyl of from 1 to 10 carbon atoms.

Representative compounds included within the scope of formula III of this invention include those set forth below:
ethyl 4-[1-(4-chlorobenzoyl)-5-methoxy-2-methyl-3-indolyl]-3-oxobutyrate ethyl 4-(5-methoxy-2-methyl-3-indolyl)-3-oxobutyrate
ethyl 4-(3-indolyl)-3-oxobutyrate
ethyl 4-[1-(4-chlorobenzoyl)-3-indolyl]-3-oxobutyrate
ethyl 4-(1-benzyl-5-methoxy-2-methyl-3-indolyl)-3-oxobutyrate.
ethyl 4-[1-(4-chlorobenzoyl)-5-methoxy-2-methyl-3-indolyl]-3-oxopentanoate
ethyl 4-[1-(4-chlorobenzoyl)-2-methyl-3-indolyl]-3-oxobutyrate
ethyl 4-[1-(3,4-dichlorobenzoyl)-5-methoxy-2-methyl-3-indolyl]-3-oxobutyrate
ethyl 4-[1-(4-chlorophenyl)-5-methoxy-2-methyl-3-indolyl]-2-methyl-3-oxobutyrate
methyl 4-[1-(4-chlorobenzoyl)-5-methoxy-2-methyl-3-indolyl]-3-oxobutyrate
methyl 4-(5-methoxy-2-methyl-3-indolyl)-3-oxobutyrate
n-butyl 4-[1-(4-chlorobenzoyl)-3-indolyl]-3-oxobutyrate
n-hexyl 4-(1-benzyl-5-methoxy-2-methyl-3-indolyl)-3-oxobutyrate
n-decyl 4-[1-(4-chlorobenzoyl)-5-methoxy-2-methyl-3-indolyl]-3-oxopentanoate
n-heptyl 4-[1-(4-chlorobenzoyl)-2-methyl-3-indolyl]]-3-oxobutyrate
n-pentyl 4-[1-(3,4-dichlorobenzoyl)-5-methoxy-2-methyl-3-indolyl]-3-oxobutyrate
t-butyl 4-[1-(4-chlorophenyl)-5-methoxy-2-methyl-3-indolyl]-2-methyl-3-oxobutyrate This invention is also directed to pharmaceutical compositions comprising a pharmaceutically inert carder and a pharmaceutically effective amount of a compound of formula I or II above. In a preferred embodiment, such pharmaceutical compositions comprise a compound of formula IV or V below:

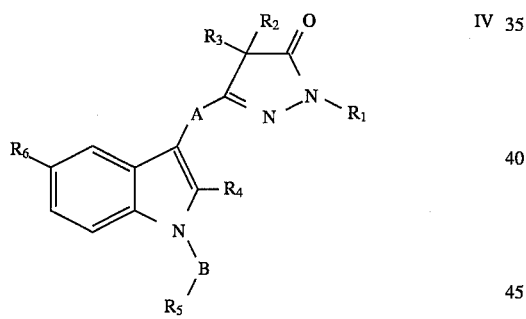

IV wherein $R_1$ is selected from the group consisting of hydrogen, alkyl of from 1 to 10 carbon atoms optionally substituted with 1 to 4 substituents selected from the group consisting of halo, aryl of from 6 to 10 carbon atoms optionally substituted with from 1 to 3 substituents selected from the group consisting of fluoro, chloro, cyano, nitro, alkyl of from 1 to 10 carbon atoms, haloalkyl of from 1 to 10 carbon atoms and at least 1 halo substituent, alkoxy of from 1 to 10 carbon atoms, cycloalkyl of from 3 to 8 carbon atoms, aryl of from 6 to 10 carbon atoms optionally substituted with from 1 to 3 substituents selected from the group consisting of fluoro, chloro, nitro, cyano, alkyl of from 1 to 10 carbon atoms, haloalkyl of from 1 to 10 carbon atoms and at least 1 halo substituent, alkoxy of from 1 to 10 carbon atoms, and $R_4$ is selected from the group consisting of hydrogen and alkyl of from 1 to 4 carbon atoms;

$R_5$ is selected from the group consisting of hydrogen, alkyl of from 1 to 10 carbon atoms optionally substituted with from 1 to 4 substituents selected from the group consisting of halo, —$NR_7R_8$, —$NR_7C(O)R_8$ where $R_7$ and $R_8$ are independently selected from the group consisting of hydrogen and alkyl of from 1 to 10 carbon atoms, aryl of from 6 to 10 carbon atoms optionally substituted with from 1 to 3 substituents selected from the group consisting of halo, cyano, nitro, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms;

$R_6$ is selected from the group consisting of halo, nitro, amino, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms;

A is selected from the group consisting of X—$R_9$— where X is selected from the group consisting of a bond, O and $S(O)_p$ where p is an integer of from 0 to 2 and $R_9$ is an alkylene group of from 1 to 6 carbon atoms; and B is selected from the group consisting of a bond, an alkylene group of from 1 to 6 carbon atoms, —$R_{10}$—Y— where $R_{10}$ is selected from the group consisting of a bond and an alkylene group of 1 to 4 carbon atoms and Y is selected from the group consisting of —C(O)— and —$S(O)_q$— where q is an integer of from 0 to 2, and —C(O)Z— where Z is selected from the group consisting of O, S, and —$NR_{11}$ where $R_{11}$ is hydrogen or alkyl of from 1 to 10 carbon atoms;

with the proviso that when $R_2$ and/or $R_3$ is hydrogen, the compounds of formula IV above can exist in the tautomeric form illustrated in formula V below:

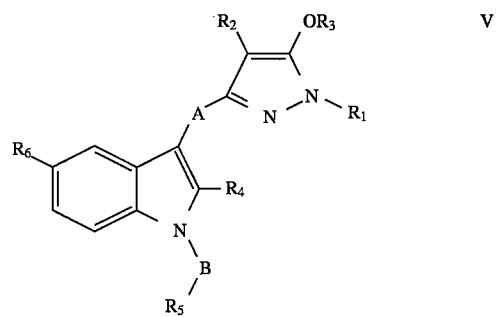

V

The pharmaceutically effective amount of a compound of formula IV is an amount effective in reducing inflammation, in inhibiting in vivo β-amyloid production, and/or inhibiting in vivo the neurotoxicity of β-amyloid to neuronal cells.

DETAILED DESCRIPTION OF THE INVENTION

As noted above, this invention is directed, in part, to novel substituted 3-indolyl-5-pyrazolone compounds as well as intermediates useful in the preparation of such substituted 3-indolyl-5-pyrazolone compounds. However, prior to describing this invention in further detail, the following terms will first be defined:

Definitions

As used herein, the following terms have the following meanings:

The term "halo" refers to fluoro, chloro, bromo and iodo. Preferred halo substituents include fluoro, chloro and bromo and, more preferably, chloro and bromo.

The term "heterocycles having from 2 to 8 carbon atoms and from 1 to 3 heteroatoms selected from the group consisting of oxygen, sulfur and nitrogen" refers to saturated and unsaturated heterocyclic groups having the requisite number of carbon atoms and heteroatoms. Suitable heterocyclic groups include, by way of example, furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, quinoxalinyl, thiadiazolyl, thiazolyl, thienyl, thiomorpholinyl (e.g. thiomorpholino), and triazolyl. These heterocyclic groups can be substituted or unsubstituted. Where the heterocyclic group is substituted, the substituent can be alkyl of from 1 to 6 carbon atoms, alkoxy of from 1 to 6 carbon atoms, and halo.

The term "β-amyloid peptide" refers to a 39–43 amino acid peptide having a molecular weight of about 4.2 kD which peptide is substantially homologous to the form of the protein described by Glenner, et al.[12] including mutations of the normal β-amyloid peptide. In whatever form, the β-amyloid peptide is an approximate 39–43 amino acid fragment of a large membrane-spanning glycoprotein, referred to as the β-amyloid precursor protein (APP). Its 43-amino acid sequence is:

1

Asp Ala Glu Phe Arg His Asp Ser Gly Tyr

11

Glu Val His His Gln Lys Leu Val Phe Phe

21

Ala Glu Asp Val Gly Ser Asn Lys Gly Ala

31

Ile Ile Gly Leu Met Val Gly Gly Val Val

41

Ile Ala Thr (SEQ ID NO: 1)

or a sequence which is substantially homologous thereto.

The term "β-amyloid inhibiting compound of formula I and/or formula II" refers to those compounds of formula I and/or II above which will inhibit the production of β-amyloid peptide. The determination of whether such compounds inhibit in vivo the production of β-amyloid peptide can be readily determined by the in vitro assay provided in Example 62 herein below.

Synthesis

The products of formula I above can be prepared by one or more of the synthetic routes described below and exemplified in the Examples.

Specifically, in reaction (1) below, indole-3-carboxylic acids (1) are converted to the corresponding keto ester derivatives (3) by reaction with a suitable dicarboxylic acid monoester, such as ethyl malonic acid (2), in a manner well known in the art[3,4]:

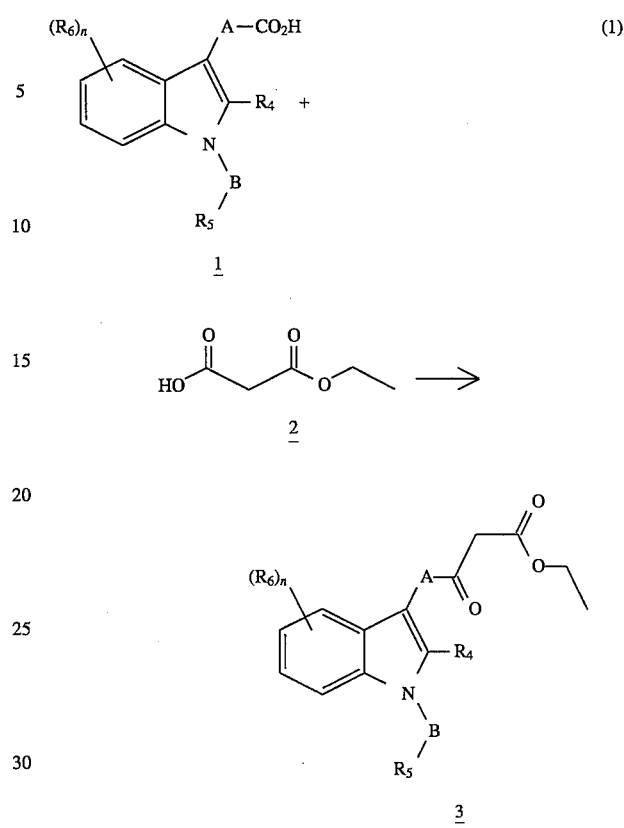

wherein $R_4$, $R_5$ and $R_6$ are as defined above. The indole-3-carboxylic acids used in this reaction are well known in the art and are disclosed, for example, by Yamamoto[7], Shen[8,10,11], and Sarett[9]. Likewise, suitable dicarboxylic acid monoesters are well known in the art and some are commercially available (e.g., ethyl malonic acid potassium salt) from Aldrich Chemical Company, Milwaukee, Wis., USA.

Reaction (1) is preferably conducted by first converting the carboxylic group of the indole-3-carboxylic acid (1) to its activated ester form by conventional methods such as by reaction with N,N'-carbonyldiimidazole. The reaction is typically conducted by employing approximately 1–2 equivalents of N,N'-carbonyldiimidizole relative to the indole-3-carboxylic acid (1) and the reaction is typically conducted at room temperature in a suitable inert diluent such as tetrahydrofuran. After confirming formation of the resulting activated ester (e.g., by t.l.c.), the activated ester can be purified by conventional means or, alternatively and preferably, is maintained in the reaction medium for subsequent use in the synthetic procedure.

In a separate reaction vessel, the dicarboxylic acid monoester, depicted in reaction (1) as ethyl malonate (2), is first converted to the corresponding magnesium enolate by reaction with, for example, at least a stoichiometric amount of isopropyl magnesium chloride. The reaction is preferably conducted in an inert solvent such as, for example, tetrahydrofuran and is preferably conducted under an inert atmosphere such as nitrogen. The reaction temperature ranges from about 0° C. to 50° C. with lower reaction temperatures preferably being employed at the start of the reaction. The reaction is typically complete within a period of from 0.5 to 10 hours with reaction completion being monitored by conventional methods, e.g., t.l.c. The reaction product is preferably maintained unrecovered in the inert solvent for subsequent me in the synthetic procedures.

The reaction is continued by dropwise adding the magnesium enolate solution to the cooled solution of the activated ester of the indole-3-carboxylic acid to provide the keto ester derivative (3). The reaction is typically conducted under an inert atmosphere at a temperature of from about 0° C. to about 30° C. with lower reaction temperatures preferably being employed at the start of the reaction. The reaction is typically complete within about 2–10 hours. After reaction completion, the reaction solution is worked up via conventional methods which typically includes the addition of a mineral acid (e.g., 1N hydrochloric acid) to effect decarboxylation of the intermediate reaction products and the resulting product is purified also by conventional methods (e.g., crystallization, chromatography, etc.) to provide or the keto ester derivative (3).

The keto ester derivative (3) can optionally be further derivatized by, for example, conventional transesterification techniques to convert the alkyl residue of the ester moiety to an alkyl residue of from 1 to 10 carbon atoms. Alternatively, the keto ester derivative (3) can be derivatized by alkylation of the methylene group of the —C(O)CH$_2$COOC$_2$H$_5$ functionality via conventional alkylation procedures. Specifically, reaction of the keto ester derivative (3) with a base, such as sodium hydride, followed by reaction with an alkyl halide, will provide for alkylation on this methylene group. Control of reaction conditions including reaction temperatures, stoichiometric amounts, etc. provide a level of control as to the degree of alkylation (monoalkylation or dialkylation). In any event, the desired product can be recovered by conventional means.

In the second step in the synthesis of the pyrazolones of this invention, the keto ester derivatives synthesized as above are then reacted with a suitable hydrazine compound (4) of the formula R$_1$—NH—NH$_2$ to provide for the compounds of formula I above using methods well known in the art[13]. Hydrazine compounds suitable for use in this reaction are well known in the art and are described, for example, by Ghali, et al.[5] and Coleman[6].

Specifically, in this reaction, keto ester (3) is contacted with at least a stoichiometric amount of hydrazine (4) in a suitable inert diluent such as dimethylformamide, ethanol, ethyl acetate, methylene chloride, mixtures of dimethylformamide and ethanol (e.g., 1:1 mixtures) and the like. The reaction is typically conducted in the presence of an excess amount of a weak base such as sodium acetate, triethylamine, and the like, or a weak acid such a p-toluenesulfonic acid, and the like, and is typically conducted at from about 0° C. to about 50° C. for from about 2 to 36 hours. After reaction completion, the reaction product is typically recovered by conventional methods such as filtration, chromatography, crystallization and the like.

The resulting pyrazolones where R$_2$ and/or R$_3$ are/is hydrogen can be further elaborated by reaction with an alkylating agent such as an alkyl halide (i.e., R$_1$X or R$_2$X where R$_1$ and R$_2$ are alkyl of from 1 to 10 carbon atoms and X is a halo group such as chloro or bromo). Specifically, the pyrazolone is first contacted with a suitable base such as an alkali metal hydride (e.g., sodium hydride) or an alkoxide (e.g., sodium methoxide) in a suitable inert solvent such as tetrahydrofuran or dimethylformamide and then at least a stoichiometric amount of the alkylating agent is added to the reaction mixture under conventional conditions to provide for pyrazolones alkylated or further alkylated at the 4 position.

Alternatively, an unsaturated substituent (=CR$_{13}$R) can be introduced at the 4 position of pyrazolones (when R$_2$ and R$_3$ are hydrogen) by reaction with an aldehyde R$_{13}$C(O)H or a ketone R$_{13}$C(O)R$_{14}$ (R$_{13}$ and R$_{14}$ are hydrogen, alkyl of from 1 to 10 carbon atoms and phenyl). Specifically, the pyrazolone is first contacted with a suitable base such as an alkali metal hydride (e.g., sodium hydride) or an alkoxide (e.g., sodium methoxide) in a suitable inert solvent such as tetrahydrofuran or dimethylformamide and then at least a stoichiometric amount of a suitable aldehyde or ketone is added to the reaction mixture under conventional conditions to provide for pyrazolones having a =CR$_{13}$R$_{14}$ substituent at the 4 position.

Utility

Compounds of Formula I and II above are useful as ultraviolet (UV) light absorbers and, accordingly, are suitable for use in compositions requiting a UV light absorbing additive, such as plastic compositions. In this regard, it is known that prolonged exposure to UV light can have a deleterious effect on the physical properties and compositional stability of certain plastics. It is, therefore, conventional to include a UV light absorbing additive in such plastic compositions and the compounds of formula I and II of this invention can be employed in this manner.

One or more of the compounds of formula I and II above can be incorporated into a mixture of polymerizable monomers employed to prepare the plastic composition such that, upon polymerization, the compound(s) is (are) homogeneously distributed throughout the composition. Alternatively, in the case of thermosetting plastics, the plastic composition can be heated to a sufficient temperature to "melt" the plastic thereby permitting incorporation of the UV light absorbing additive therein. In this latter embodiment, the additive is typically uniformly mixed into the composition prior to cooling.

In another embodiment, the compositions are mixed with a polymerizable material and coated onto a core plastic material where, upon curing, a UV absorbing coating is formed over the plastic material. The polymerizable material employed with this coating is preferably an organic monomer such a reactive ethylene containing molecule (e.g., methyl acrylate, methyl methacrylate, etc.) and is preferably the same organic monomer or mixture of monomers employed to prepare the plastic composition.

The UV absorbing additive of formula I and II above is typically employed in the plastic composition or in the coating in sufficient amount to absorb at least a portion, and preferably at least a majority, of the UV light to which the plastic composition will be exposed to under typical in-use conditions. See, for example, U.S. Pat. No. 5,162,825 which is incorporated herein by reference in its entirety. Preferably, the plastic composition or coating will contain from about 0.01 to about 1 weight percent of the UV light absorbing additive of this invention based on the total weight of the composition or coating.

The compounds of formula I and II above, preferably those of formula IV, also possess pharmaceutical utility as anti-inflammatory agents. Specifically, in vitro assays establish that the anti-inflammatory compounds of this invention inhibit 5-lipoxygenase activity which inhibition is well documented to correlate to anti-inflammatory activity.[14,15] The determination of whether a compound of formula I or II possess anti-inflammatory activity in vivo can be determined in vitro by an assay measuring the degree of 5-lipoxygenase inhibition as set forth in Example 64 hereinbelow. Such in vitro assays are well documented in the art to correlate to in vivo utility as anti-inflammatory agents[14]. Accordingly, this invention is also directed to a method for reducing the degree of intimation in a mammal which method comprises administering to said mammal an anti-inflammatory effective amount of at least one inflammation reducing compound of formula I and/or II above.

Certain of the compounds of formula I and II above, preferably those of formula IV (where $R^1$ is not hydrogen), also have been shown via in vitro assays to inhibit β-amyloid peptide production in mammalian cells. Such compounds can, therefore, be administered to a mammal in order to inhibit the production and subsequent deposition of amyloid plaques well documented to be associated with pathogenesis of Alzheimer's as well as other β-amyloid peptide related conditions, including, by way of example only, Down's syndrome, Hereditary Cerebral Hemorrhage with Amyloidosis (HCHWA-D), advanced aging of the brain, and the like. The determination of whether such compounds inhibit in vivo the production of β-amyloid peptide can be readily determined by the in vitro assay provided in Example 62 herein below. Accordingly, this invention is also directed to a method for inhibiting β-amyloid production in a mammal which method comprises the administration to said mammal of an effective amount of a β-amyloid inhibiting compound of formula I and/or formula II and preferably of formula IV where $R^1$ is not hydrogen.

Again, certain of the compounds of formula I and II above, preferably those of formula IV, also have been shown via in vitro assays to inhibit the neurotoxicity of β-amyloid peptide against neuronal cells, including human neuronal cells. The determination of whether such compounds inhibit in vivo the neurotoxicity of β-amyloid peptide can be readily determined by the in vitro assay provided in Example 63 herein below. Accordingly, this invention is also directed to a method for inhibiting the neurotoxicity of β-amyloid production in a mammal which method comprises the administration of an effective amount of a neurotoxicity inhibiting compound of formula I and/or formula II, and preferably of formula IV, where $R^1$ is preferably hydrogen.

In still a further embodiment, the compounds of formula I and/or II, and preferably of formula IV and/or V, can be used prophylactically or therapeutically in preventing/retarding the onset of Alzheimer's disease or for treating a patient with Alzheimer's disease. In one such embodiment, this invention is directed to a method for retarding the onset of Alzheimer's disease in a human patient susceptible to Alzheimer's disease which method comprises administering to said patient prior to the onset of Alzheimer's disease a pharmaceutically effective amount of a compound of formula I and/or II and preferably of formula IV and/or V. In another such embodiment, this invention is directed to a method for treating a human patient with Alzheimer's disease which method comprises administering to said patient a pharmaceutically effective amount of a compound of formula I and/or II and preferably of formula IV and/or V so as to retard further clinically development of Alzheimer's disease in said patient.

Pharmaceutical Formulations

When employed as pharmaceuticals, the compounds of formula I and II, preferably those of formula IV and V, above are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of formula I and/or II, and preferably of formula IV and/or V, above associated with pharmaceutically acceptable carriers. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared rising the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation Example 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| Active Ingredient | 50.0 mg |
| Xanthan gum | 4.0 mg |
| Sodium carboxymethyl cellulose (11%) | 50.0 mg |
| Microcrystalline cellulose (89%) | |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

| Ingredient | Quantity (mg/capsule) |
| --- | --- |
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 560 mg quantities.

Formulation Example 9

An intravenous formulation may be prepared as follows:

| Ingredient | Quantity |
| --- | --- |
| Active Ingredient | 250.0 mg |
| Isotonic saline | 1000 ml |

Formulation Example 10

A topical formulation may be prepared as follows:

| Ingredient | Quantity |
| --- | --- |
| Active Ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e,g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drag latentiation by the conversion of hydrophilic drags into lipid-soluble drugs. Latentiation is generally achieved through blocking of the hydroxy, carbonyl, sulfate, and primary amine groups present on the drag to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The following synthetic, UV, and biological examples are offered to illustrate this invention and are not to be construed in any way as limiting the scope of this invention. Unless otherwise stated all temperatures are in degrees Celsius. Also, in these examples, unless otherwise defined below, the abbreviations employed have their generally accepted meaning:

| | |
| --- | --- |
| bd | = broad doublet |
| bs | = broad singlet |
| cm | = centimeter |
| $^{13}$C-NMR | = $C^{13}$ nuclear magnetic resonance |
| d | = doublet |
| dd | = doublet of doublets |
| dt | = doublet of triplets |
| g | = gram |
| $^1$H-NMR | = proton nuclear magnetic resonance |
| Hz | = Hertz |

-continued

| | |
|---|---|
| LRMS(FAB) | = low resolution mass spectroscopy |
| m | = multiplet |
| M | = molar |
| mg | = milligram |
| mL | = milliliter |
| mmol | = millimol |
| mp | = melting point |
| N | = normal |
| ng | = nanograms |
| nm | = nanometers |
| OD | = optical density |
| psi | = pounds per square inch |
| q | = quartet |
| rpm | = rotations per minute |
| s | = singlet |
| t | = triplet |
| μL | = microliters |
| μM | = micromolar |
| UV | = ultraviolet |

Examples 1–60 illustrate synthetic methods employed to prepare numerous compounds within the scope of this invention. Example 66 illustrates that representative compounds of this invention are capable of absorbing ultraviolet (UV) light and, accordingly, are suitable for use in compositions requiting a UV light absorbing additive, such as plastic compositions. Examples 67–69 illustrate biological data establishing the efficacy of certain of the compositions of this invention in reducing the human neuronal toxicity of β-amyloid peptide and/or in inhibiting cellular expression of β-amyloid peptide.

EXAMPLES

Example 1

Synthesis of ethyl 4-[1-(4-chlorobenzoyl)-5-methoxy-2-methyl-3-indolyl]-3-oxobutyrate 1-(4-Chlorobenzoyl)-5-methoxy-2-methyl-3-indoleacetic acid (1.00 g, 2.79 mmol) was dissolved in 20 mL of dry tetrahydrofuran under nitrogen at room temperature in the presence of N,N'-carbonyldiimidazole (543 mg, 3.34 mmol) and stirred for 12 hours. Ethyl hydrogen malonate (553 mg, 4.18 mmol) dissolved in 15 mL of tetrahydrofuran was reacted with isopropyl magnesium chloride (4.18 mL of a 2M solution in tetrahydrofuran) at 0° C. for 30 minutes and then at room temperature for 45 minutes and at 40° to 50° C. for 30 minutes under $N_2$. This solution of the magnesium enolate was added dropwise with stirring to the cooled imidazolide solution. The resulting mixture was, after warming to room temperature, stirred for 5 hours and then poured into cold 1N hydrochloric acid. Ethyl acetate was added and the organic layer washed with brine, dried over $MgSO_4$, and evaporated to give the crude β-keto ester as an oil. Crystallization from ethyl acetate/hexanes affords the title compound as a pale yellow solid: mp. 89° to 92° C.; $^1$H-NMR (CDCl$_3$) δ=7.66 (d, 2H, J=8.25 Hz), δ=7.50 (d, 2H, J=8.16 Hz), δ=6.88 (d, 2H, J=8.79 Hz), δ=6.67 (bd, 1H, J=8.91 Hz), δ=4.17 (q, 2H, J=7.14 Hz), δ=3.87 (s, 2H), 3.83 (s, 3H), δ=3.47 (s, 2H), δ=2.37 (s, 3H), δ=1.25 (t, 3H, J=7.14 Hz); $^{13}$C-NMR (CDCl$_3$) δ=200.40, 168.84, 167.64, 156.75, 139.99, 136.93, 134.28, 131.78, 131.42, 131.02, 129.74, 115.63, 112.45, 112.22, 101.55, 62.09, 56.06, 48.50, 14.65, 13.94; LRMS (FAB) 427.1 (M+H$^+$).

The keto esters described in Examples 2 through 7 and 38, 48, 50, 52, 54, 56 and 59 below were prepared in a manner similar to Example 1 above with appropriate substitution of starting materials.

Example 2

Synthesis of ethyl 4-(5-methoxy-2-methyl-3-indolyl)-3-oxobutyrate

Ethyl 4-(5-methoxy-2-methyl-3-indolyl)-3-oxobutyrate was prepared in a manner similar to that described above for Example 1. $^1$H-NMR (CDCl$_3$) δ=8.23 (s, 1H), 7.18 (d, 1H, J=8.43 Hz), 6.90 (s, 1H), 6.78 (d, 1H, J=8.43 Hz), 4.15 (q, 2H), 3.88 (s, 3H), 3.82 (s, 2H), 3.42 (s, 2H), 2.32 (s, 3H) 1.25 (t, 3H).

Example 3

Synthesis of ethyl 4-(3-indolyl)-3-oxobutyrate

Ethyl 4-(3-indolyl)-3-oxobutyrate was prepared in a manner similar to that described above for Example 1. $^1$H-NMR (CDCl$_3$) δ=8.50 (bs, 1H), 7.55 (d, 1H, J=8.45 Hz), 7.33 (d, 1H, J=8.44 Hz), 7.19 (m, 21H), 7.02 (s, 1H), 4.15 (q, 2H), 3.93 (s, 2H), 3.50 (s, 2H), 1.25 (t, 3H); $^{13}$C-NMR (CDCl$_3$) δ=202.55, 167.90, 136.67, 127.58, 124.46, 122.47, 120.20, 118.50, 111.96, 107.42, 61.70, 47.79, 40.40, 13.99.

Example 4

Synthesis of ethyl 4-[1-(4-chlorobenzoyl)-3-indolyl]-3-oxobutyrate

Ethyl 4[1-(4-chlorobenzoyl)-3-indolyl]-3-oxobutyrate was prepared in a manner similar to that described above for Example 1. $^1$H-NMR (CDCl$_3$) δ=8.38 (d, 1H, J=7.83 Hz), δ=7.70 (d, 2H, J=7.38 Hz), δ=7.53 (d, 4H, J=9.72 Hz), δ=7.38 (m, 2H), δ=4.16 (q, 2H, J=4.56 Hz), δ=3.92 (s, 2H), δ=3.51 (s, 2H), δ=1.25 (t, 3H, J=4.56 Hz); $^{13}$C-NMR (CDCl$_3$) δ=200.05, 175.92, 173.14, 167.87, 167.58, 138.98, 136.82, 133.29, 131.20, 129.60, 126.72, 126.27, 124.71, 119.51, 117.12, 114.69, 90.69, 62.15, 48.97, 39.90, 14.78; LRMS (FAB) 383.1 (M$^+$).

Example 5

Synthesis of ethyl 4-(1-benzyl-5-methoxy-2-methyl-3-indolyl)-3-oxobutyrate

Ethyl 4-(1-benzyl-5-methoxy-2-methyl-3-indolyl)-3-oxobutyrate was prepared in a manner similar to that described above for Example 1. $^1$H-NMR (CDCl$_3$) δ=7.25 (m, 2H), 7.10 (d, 1H, J=8.45 Hz), 6.98 (m, 2H), 6.78 (m, 1H), 5.30 (s, 2H), 4.16 (q, 2H), 3.88 (s, 3H), 3.85 (s, 3H), 3.40 (s, 2H), 2.30 (s, 3H).

Example 6

Synthesis of ethyl 4-[1-(4-chlorobenzoyl)-5-methoxy-2-methyl -3-indolyl]-3-oxopentanoate Ethyl 4-[1-(4-chlorobenzoyl)-5-methoxy-2-methyl-3-indolyl]-3-oxopentanoate was prepared in a manner similar to that of Example 1 above. $^1$H-NMR (CDCl$_3$) δ=7.66 (d, 2H, J=8.25 Hz), δ=7.50 (d, 2H, J=8.16 Hz), δ=6.88 (d, 2H, J=8.79 Hz), δ=6.67 (bd, 1H, J=8.91 Hz), δ=4.17 (q, 2H, J=7.14 Hz), δ=3.83 (s, 3H), 3.2 (s, 2H), δ=2.8 (m, 2H), δ=2.6(m, 2H), δ=2.3 (s, 3H), δ=1.25 (t, 3H, J=7.14 Hz); $^{13}$C-NMR (CDCl$_3$) δ=200.40, 168.84, 167.64, 156.75, 139.99, 136.93, 134.28, 131.78, 131.42, 131.02, 129.74, 115.63, 112.45, 112.22, 101.55, 62.09, 56.06, 48.50, 14.65, 13.94.

Example 7

Synthesis of ethyl 4-[1-(4-chlorobenzoyl)-2-methyl-3-indolyl]-3-oxobutyrate

Ethyl 4-[1-(4-chlorobenzoyl)-2-methyl-3-indolyl]-3-oxobutyrate was prepared in a manner similar to that of Example 1 above. $^1$H-NMR (CDCl$_3$) δ=7.66 (d, 2H, J=8.25 Hz), δ=7.50 (d, 2H, J=8.16 Hz), δ=6.88 (d, 2H, J=8.79 Hz), δ=6.67 (bd, 1H, J=8.91 Hz), δ=4.17 (q,2H, J=7.14 Hz), δ=3.5 (s, 2H), δ=3.2 (s, 2H), δ=2.3 (s, 3H), δ=1.25 (t, 3H, J=7.14 Hz); $^{13}$C-NMR (CDCl$_3$) δ=200.40, 168.84, 167.64, 156.75, 139.99, 136.93, 134.28, 131.78, 131.42, 131.02, 129.74, 115.63, 112.45, 112.22, 101.55, 62.09, 56.06, 48.50, 14.65, 13.94.

Example 8

Synthesis of 3-[1-(4-clorobenzoyl)-5-methoxy-2-methyl-3-indolylmethyl]-1-phenyl- 5-pyrazolone A solution of the keto ester from Example 1 (192 mg, 0.45 mmol) in 11 mL of EtOH/DMF (10:1) was stirred at room temperature for 15 hours with NaOAc (110 mg, 1.35 mmol) and phenylhydrazine hydrochloride (98 mg, 0.67 mmol). The solvents were removed and the crude residue partitioned between EtOAc and brine. The organic layer was dried over MgSO$_4$, evaporated and the crude material purified on column chromatography (silica gel) eluting with ethyl acetate/hexanes (1:7). The desired material was isolated as a solid; mp: 148° to 150° C.; $^1$H-NMR (CDCl$_3$) δ=7.89 (d, 2H, J=8.40 Hz), δ=7.68 (d, 2H, J=8.49 Hz), δ=7.50 (d, 2H, J=8.49 Hz), δ=7.40 (t, 2H, J=8.01 Hz), δ=7.19 (t, 1H, J=7.50 Hz), δ=7.00 (d, 1H, J=2.43 Hz), δ=6.85 (d, 1H, J=9.03 Hz), δ=6.69 (dd, 1H, J=2.43, 9.03 Hz), δ=3.89 (s, 2H), 3.81 (s, 3H), δ=3.36 (s, 2H), δ=2.46 (s, 3H); $^{13}$C-NMR (CDCl$_3$) δ=170.94, 168.88, 158.08, 156.54, 139.75, 138.55, 136.15, 133.92, 131.52, 131.18, 129.64, 129.30, 125.53, 119.18, 115.59, 112.50, 101.70, 56.29, 41.73, 27.16, 13.79; LRMS (FAB) 472.2 (M+H$^+$); Rf 0.56 (silica gel, EtOAc/hexanes 1:1).

Using the procedure in Example 8, the pyrazolones described in Examples 9–22 are prepared.

Example 9

Synthesis of 3-[1-(4-chlorobenzoyl)-5-methoxy-2-methyl-3-indolylmethyl]-1-cyclohexyl- 5-pyrazolone The title compound was prepared by contacting the keto ester from Example 1 and cyclohexylhydrazine hydrochloride. m.p. 187° to 188.5° C.; $^1$H-NMR (CDCl$_3$) δ=7.67 (d, 2H, J=8.49 Hz), δ=7.49 (d, 2H, J=8.43 Hz), δ=6.93 (d, 1H, J=2.37 Hz), δ=6.84 (d, 1H, J=5.61 Hz), δ=6.69 (dd, 1H, J=2.43, 8.91 Hz), δ=4.05 (m, 1H), δ=3.81 (s, 3H), δ=3.78 (s, 2H), δ=3.09 (s, 2H), δ=2.40 (s, 3H), δ=1.83–1.45 (m, 10H); $^{13}$C-NMR (CDCl$_3$) δ=171.77, 168.65, 156.89, 156.34, 135.77, 133.56, 131.73, 130.63, 129.52, 115.38, 114.09, 112.07, 101.24, 56.05, 52.56, 40.81, 31.44, 27.40, 25.93, 25.74, 13.62; LRMS (FAB) 478.4 (M+H$^+$); Rf 0.30 (silica gel, EtOAc/hexanes 1:1).

Example 10

Synthesis of 3-[1-(4-chlorobenzoyl)-5-methoxy-2-methyl-3-indolylmethyl]-1-cyclobutyl- 5-pyrazolone The title compound was obtained starting with the keto ester from Example 1 and cyclobutylhydrazine hydrochloride. $^1$H-NMR (CDCl$_3$) δ=7.67 (d, 2H, J=7.08 Hz), δ=7.49 (d, 2H, J=7.05 Hz), δ=6.99 (bd, 1H), δ=6.84 (d, 1H, J=9.03 Hz), δ=6.69 (bd, 1H, J=9.06 Hz), δ4.71 (m, 1H), 3.82 (s, 5H), δ=3.10 (s, 2H), δ=2.46 (m, 1H), δ=2.42 (s, 3H), δ=2.23 (m, 2H), δ=2.15 (m, 4H); $^{13}$C-NMR (CDCl$_3$) δ=171.55, 168.83, 157.07, 156.63, 140.04, 135.98, 134.24, 131.74, 131.40, 130.82, 129.77, 115.67, 114.19, 112.48, 101.47, 56.21, 47.82, 40.98, 31.53, 29.12, 27.31, 15.43, 13.75; LRMS (FAB)450.1 (M+H$^+$); Rf 0.33 (silica gel, EtOAc/hexanes 1:1).

Example 11

Synthesis of 3-[1-(4-chlorobenzoyl)-5-methoxy-2-methyl-3-indolylmethyl]-1-cyclopentyl- 5-pyrazolone The title compound was obtained starting with the keto ester from Example 1 and cyclopentylhydrazine hydrochloride. m.p. 153° to 155° C.; $^1$H-NMR (CDCl$_3$) δ=7.67 (d, 2H, J=8.49 Hz), δ=7.49 (d, 2H, J=8.49 Hz), δ=6.93 (s, 1H), δ=6.84 (d, 1H, J=9.00 Hz), δ=6.69 (d, 1H, J=2.49 Hz), δ=4.59 (m, 1H), δ=3.81 (s, 3H), δ=3.78 (s, 2H), δ=3.10 (s, 2H), δ=2.41 (s, 3H), δ=1.93–1.79 (m, 6H), δ=1.63 (m, 2H); $^{13}$C-NMR (CDCl$_3$) δ=172.01, 168.82, 157.05, 156.63, 140.02, 135.93, 134.26, 131.74, 131.40, 130.88, 129.76, 115.66, 114.27, 112.51, 101.44, 56.20, 54.40, 40.83, 31.07, 27.31, 25.07, 13.73; Rf 0.35 (silica gel, EtOAc/hexanes 1:1).

Example 12

Synthesis of 3-[1-(4-chlorobenzoyl)-5-methoxy-2-methyl-3-indolylmethyl]-1-cycloheptyl- 5-pyrazolone The title compound was obtained starting with the keto ester from Example 1 and cycloheptylhydrazine hydrochloride. m.p. 145° to 148° C.; $^1$H-NMR (CDCl$_3$) δ=7.67 (d, 2H, J=8.37 Hz), δ=7.50 (d, 2H, J=8.43 Hz), δ=6.93 (bs, 1H), 6.84 (d, 1H, J=9.09 Hz), δ=6.69 (d, 1H, J=2.31, 9.03 Hz), δ=4.21 (m, 1H), δ=3.82 (s, 3H), δ=3.78 (s, 2H), δ=3.07 (s, 2H), δ=2.41 (s, 3H), δ=1.91–1.72 (m, 6H), 1.61–1.47 (m, 6H); $^{13}$C-NMR (CDCl$_3$) δ=171.34, 168.82, 157.04, 156.63, 140.02, 136.05, 134.26, 131.74, 131.40, 130.83, 129.76, 115.65, 114.30, 112.50, 101.46, 56.20, 54.84, 40.60, 33.99, 28.56, 27.32, 25.26, 13.35; Rf 0.36 (silica gel, EtOAc/hexanes 1:1).

Example 13

Synthesis of 3-[1-(4-chlorobenzoyl)-5-methoxy-2-methyl-3-indolylmethyl]-1-benzyl- 5-pyrazolone The title compound was obtained starting with the keto ester from Example 1 and benzylhydrazine hydrochloride. The desired product was isolated as an oil. $^1$H-NMR (CDCl$_3$) δ=7.70 (d, 2H, J=8.50 Hz), δ=7.45 (d, 2H, J=8.50

Hz), δ=7.36 (m, 5H), δ=6.82 (m, 2H), δ=6.63 (d, 1H, J=9.02 Hz), δ=4.82 (s, 2H), δ=3.78 (s, 2H), δ=3.70 (s, 3H), δ=3.15 (s, 2H), δ=2.41 (s, 3H).

Example 14

Synthesis of 3-[1-(4-chlorobenzoyl)-5-methoxy-2-methyl-3-indolylmethyl]-1-t-butyl- 5-pyrazolone The title compound was obtained starting with the keto ester from Example 1 and t-butylhydrazine hydrochloride. The desired material was isolated as an oil. $^1$H-NMR (CDCl$_3$) δ=7.65 (d, 2H, J=8.46 Hz), δ=7.44 (d, 2H, J=8.46 Hz), δ=6.95 (bs, 1H), δ=6.82 (d, 1H, J=9.06 Hz), δ=6.68 (bd, 1H, J=9.00 Hz), δ=3.82 (s, 3H), δ=3.61 (s, 2H), δ=3.08 (s, 2H), δ=2.42 (s, 3H), δ=1.42 (s, 9H).

Example 15

Synthesis of 3-[1-(4-chlorobenzoyl)-5-methoxy-2-methyl-3-indolylmethyl]-5-pyrazolone The title compound was obtained starting with the keto ester from Example 1 and hydrazine dihydrochloride. m.p. >230° C.; $^1$H-NMR (DMSO-d$_6$) δ=7.68 (q, 4H, J=8.61 Hz), δ=6.99 (d, 1H, J=2.19 Hz), δ=6.89 (d, 1H, J=10.56 Hz), δ=6.71 (dd, 1H, J=2.31, 8.97 Hz), δ=3.86 (s, 2H), δ=3.73 (s, 3H), δ=2.24 (s, 3H); LRMS (FAB) 396.1 (M$^+$); Rf 0.07 (silica gel, EtOAc/hexanes 1:1).

Example 16

Synthesis of 3-[1-(4-chlorobenzoyl)-5-methoxy-2-methyl-3-indolylmethyl]-1-( 4-heptyl)-5-pyrazolone The title compound was obtained starting with the keto ester from Example 1 and 4-heptylhydrazine hydrochloride. m.p. 167° C. to 168° C.

Example 17

Synthesis of 3-(5-methoxy-2-methyl-3-indolylmethyl)-1-cyclohexyl-5-pyrazolone

The title compound was obtained starting with the keto ester from Example 2 and cyclohexylhydrazine hydrochloride. m.p. 99° to 101° C.; $^1$H-NMR (CDCl$_3$) δ=7.75 (bs, 1H), δ=7.15 (d, 1H, J=8.73 Hz), δ=6.93 (d, 1H, J=2.46 Hz), δ=6.80 (dd, 1H, J=2.37, 8.67 Hz), δ=4.15 (m, 1H), δ=3.83 (s, 3H), δ=3.76 (s, 2H), δ=3.06 (s, 2H), δ=2.39 (s, 3H), δ=1.86–1.72 (m, 5H), δ=1.42–1.25 (m, 6H); $^{13}$C-NMR (CCl$_3$) δ=172.05, 158.71, 154.57, 133.12, 130.41, 128.79, 111.85, 106.26, 100.49, 56.51, 52.73, 40.65, 31.64, 27.31, 26.23, 25.51, 11.99; LRMS (FAB) 340.4 (M+H$^+$); Rf 0.14 (silica gel, EtOAc/hexanes 1:1). Elemental Analysis: C=70.84%, H=7.43%, and N=12.16%.

Example 18

Synthesis of 3-(3-indolylmethyl)-1-cyclohexyl-5-pyrazolone

The title compound was obtained starting with the keto ester from Example 3 and cyclohexylhydrazine hydrochloride. m.p. 192° to 194° C.; $^1$H-NMR (CDCl$_3$) δ=8.24 (bs, 1H), δ=7.59 (d, 1H, J=7.80 Hz), δ=7.40 (d, 1H, J=7.85 Hz), δ=7.27–7.09 (m, 3H), δ=4.05 (m, 1H), δ=3.86 (s, 2H), δ=3.11 (s, 2H), δ=1.88–1.68 (m, 6H), δ=1.40–1.25 (m, 4H); $^{13}$C-NMR (CDCl$_3$) δ=172.13, 158.39, 136.83, 127.36, 123.09, 120.12, 119.19, 111.94, 110.83, 52.68, 40.60, 31.87, 28.34, 25.74, 25.37; LRMS (FAB) 296.2 (M$^+$); Rf 0.14 (silica gel, EtOAc/hexanes 1:1).

Example 19

Synthesis of 3-[1-(4-chlorobenzoyl)-3-indolylmethyl]-1-cyclohexyl-5-pyrazolone

The title compound was obtained starting with the keto ester from Example 4 and cyclohexylhydrazine hydrochloride. m.p. 109° to 111° C.; $^1$H-NMR (CDCl$_3$) δ=8.37 (d, 1H, J=8.07 Hz), δ=7.70 (d, 2H, J=8.43 Hz), δ=7.54 (m, 2H), δ=7.40 (m, 2H), δ=7.24 (d, 1H, J=7.32 Hz), δ=3.95 (m, 1H), δ=3.80 (s, 2H), δ=3.14 (s, 2H), δ=1.86–1.63 (m, 6H), δ=1.39–1.26 (m, 4H); LRMS (FAB) 434.3 (M+H$^+$); Rf 0.40 (silica gel, EtOAc/hexanes 1:1).

Example 20

Synthesis of 3-(1-benzyl-5-methoxy-2-methyl-3-indolylmethyl)-1-cyclohexyl-5-pyrazolone The title compound was obtained starting with the keto ester from Example 5 and cyclohexylhydrazine hydrochloride. m.p. 102° to 105° C.; $^1$H-NMR (CDCl$_3$) δ=7.22 (m, 4H), δ=7.09 (d, 1H, J =9.06 Hz), δ=6.97 (bds, 1H), δ=6.89 (d, 1H, J=8.86 Hz), δ=6.77 (d, 1H, J=9.06 Hz), δ=5.28 (s, 2H), δ=4.00 (m, 1H), δ=3.82 (s, 3H), δ=3.81 (s, 2H), δ=3.06 (s, 2H), δ=2.29 (s, 3H), δ=1.76–1.59 (m, 6H), δ=1.29 (m, 4H); $^{13}$C-NMR (CDCl$_3$) δ=171.82, 158.80, 154.96, 138.28, 134.80, 132.05, 129.48, 128.38, 127.83, 126.19, 111.71, 110.24, 105.84, 100.53, 56.18, 52.51, 47.20, 40.79, 31.45, 27.59, 25.94, 25.78, 10.87; LRMS (FAB) 430.4 (M+H$^+$); Rf 0.40 (silica gel, EtOAc/hexanes 1:1).

Example 21

Synthesis of 3-[1-(4-chlorobenzoyl)-5-methoxy-2-methyl-3-indolylethyl]- 1-cyclohexyl-5-pyrazolone The title compound was obtained starting with the keto ester from Example 6 and cyclohexylhydrazine hydrochloride. m.p. 110° C.; H-NMR (CDCl$_3$): δ7.67 (d, 2H, J=8.49 Hz), δ=7.49 (d, 2H, J=8.43 Hz), δ=6.93 (d, 1H, J=2.37 Hz), δ=6.84 (d, 1H, J=5.61 Hz, δ=6.69 (dd, 1H, J=2.43, 8.91 Hz), δ=4.05 (m, 1H), δ=3.81 (s, 3H), δ=3.3 (s, 2H), δ=2.9 (m, 2H), δ=2.7 (m, 2H), δ=2.4 (s, 3H), δ=1.83–1.45 (m, 10H); $^{13}$C-NMR (CDCl$_3$) δ=171.77, 168.65, 156.89, 156.34, 135.77, 133.56, 131.73, 130.63, 129.52, 115.38, 114.09, 112.07, 101.24, 56.05, 52.56, 40.81, 31.44, 27.40, 25.93, 25.74, 13.62; LRMS (FAB) 492.4 (M+H$^+$); Rf 0.30 (silica gel, EtOAc/hexanes 1:1).

Example 22

Synthesis of 3-[1-(4-chlorobenzoyl)-2-methyl-3-indolylmethyl]-1-cyclohexyl-5-pyrazolone The title compound was obtained starting with the keto ester from Example 7 and cyclohexylhydrazine hydrochloride. m.p. 98° C.; $^1$H-NMR (CDCl$_3$) δ=7.67 (d, 2H, J=8.49

Hz), δ=7.49 (d, 2H, J=8.43 Hz), δ=6.93 (d, 1H, J=2.37 Hz), δ=6.84 (d, 1H, J=5.61 Hz), δ=6.69 (dd, 1H, J=2.43, 8.91 Hz), δ=4.05 (m, 1H), δ=3.78 (s, 2H), δ=3.09 (s, 2H), δ=2.40 (s, 3H), δ=1.83–1.45 (m, 10H); $^{13}$C-NMR (CDCl$_3$) δ=171.77, 168.65. 156.89, 156.34, 135.77, 133.56, 131.73, 130.63, 129.52, 115.38, 114.09, 112.07, 101.24, 56.05, 52.56, 40.81, 31.44, 27.40, 25.93, 25.74, 13.62; LRMS (FAB) 448.4 (M+H$^+$); Rf 0.40 (silica gel, EtOAc/hexanes 1:1).

Example 23

Synthesis of 3-[1-(4-chlorobenzoyl)-5-methoxy-2-methyl-3-indolylmethyl]-1-(4-methoxyphenyl)-5-pyrazolone Keto ester from Example 1 (500 mg, 1.16 mmol) in 10 mL of dry tetrahydrofuran was stirred at room temperature with triethylamine (489 μL, 3.48 mmol) and 4-methoxyphenylhydrazine hydrochloride (224 mg, 1.16 mmol) overnight under N$_2$. The solvent was removed and the crude residue partitioned between ethyl acetate and brine. The organic layer was dried over MgSO$_4$. After filtration and evaporation of the solvent, the crude material was eluted over silica gel with ethyl acetate/hexanes (1:2) to afford the desired material as a solid. m.p. 101° to 103° C.; $^1$H-NMR (CDCl$_3$) δ=7.75 (d, 2H, J=9.06 Hz), δ=7.68 (d, 2H, J=8.28 Hz), δ=7.50 (d, 2H, J=8.52 Hz), δ=6.99 (d, 1H, J=2.43 Hz), δ=6.94 (d, 2H, J=9.06 Hz), δ=6.82 (d, 1H, J=9.06 Hz), δ=6.70 (d, 1H, J=9.06 Hz), δ=3.88 (s, 2H), δ=3.82 (s, 3H), δ=3.81 (s, 3H), δ3.33 (s, 2H), δ=2.45 (s, 3H); $^{13}$C-NMR (CDCl$_3$) δ=170.59, 168.83, 157.97, 157.62, 156.68, 140.08, 136.25, 134.20, 131.89, 131.76, 131.44, 130.78, 129.79, 121.35, 115.71, 114.56, 113.83, 112.34, 101.63, 56.27, 56.07, 41.71, 27.19, 13.83; LRMS (FAB) 502.2 (M+H$^+$); Rf 0.38 (silica gel, EtOAc/hexanes 1:1).

Example 24

Synthesis of 3-[1-(4-chlorobenzoyl)-5-methoxy-2-methyl-3-indolylmethyl]-1-(3-methoxyphenyl)-5-pyrazolone The title compound was obtained starting with the keto ester from Example 1 and 3-methoxyphenylhydrazine hydrochloride following the procedure described in Example 23. m.p. 102° to 104° C.; $^1$H-NMR (CDCl$_3$) δ=7.69 (bd, 2H) δ=7.51 (bd, 4H), δ=7.30 (d, 1H, J=8.10 Hz) δ=7.00 (s, $^1$H) δ=6.86 (d,1H, J=8.73 Hz) δ=6.74 (m, 2H), δ=3.89 (s, 2H) δ=3.84 (s, 3H) δ=3.82 (s, 3H) δ=3.36 (s, 2H), δ=2.46 (s, 3H); $^{13}$C-NMR (CDCl$_3$) δ=170.84, 168.83, 160.53, 158.02, 156.68, 140.09, 140.01, 136.27, 134.19, 131.76, 131.44, 130.76, 130.23, 129.79, 115.70, 113.72, 112.33, 111.59, 105.05, 101.65, 56.26, 55.94, 41.99, 27.19, 27.19, 13.83; LRMS (FAB) 502.1 (M+H$^+$); Rf 0.48 (silica gel, EtOAc/hexanes 1:1).

Example 25

Synthesis of 3-[1-(4-chlorobenzoyl)-5-methoxy-2-methyl-3-indolylmethyl]-1-(3-trifluoromethylphenyl)-5-pyrazolone The title compound was obtained starting with the keto ester from Example 1 and 3-trifluoromethylphenylhydrazine hydrochloride following the procedure described in Example 23. The desired material was isolated as an oil. $^1$H-NMR (CDCl$_3$) δ=8.16 (bs, 2H), δ=7.67 (d, 2H, J=8.46 Hz) δ=7.49 (m, 4H) δ=7.01 (s, 1H) δ=6.85 (d, 1H, J=9.09 Hz), δ=6.67 (d, 1H, J=9.03 Hz) δ=3.90 (s, 2H) δ=3.84 (s, 3H) δ=3.39 (s, 2H) δ=2.46 (s, 3H); $^{13}$C-NMR (CDCl$_3$) δ=170.93, 168.81, 158.77, 156.72, 140.11, 139.08, 136.30, 134.15, 132.02, 131.74, 131.59, 130.69, 130.03, 129.79, 126.28, 121.95, 121.05, 115.74, 113.48, 112.45, 101.55, 56.20, 41.87, 27.16, 13.78; LRMS (FAB) 540.0 (M$^+$); Rf 0.58 (silica gel, EtOAc/hexanes 1:1).

Example 26

Synthesis of 3-[1-(4-chlorobenzoyl)-5-methoxy-2-methyl-3-indolylmethyl]-1-(3-chlorophenyl)-5-pyrazolone The title compound was obtained starting with the keto ester from Example 1 and 3-chlorophenylhydrazine hydrochloride following the procedure described in Example 23. m.p. 148° to 150° C.; $^1$H-NMR (CDCl$_3$) δ=7.94 (bs, 1H), δ=7.86 (d, 1H, J=8.22 Hz), δ=7.68 (d, 2H, J=8.49 Hz), δ=7.49 (d, 2H, J=8.49 Hz), δ=7.33 (t, 1H, J=8.13 Hz), δ=7.16 (bs, 1H), δ=6.99 (d, 1H, J=2.43 Hz), δ=6.85 (d, 1H, J=8.97 Hz), δ=6.70 (dd, 1H, J=2.52, 9.03 Hz), δ=3.88 (s, 2H), δ=3.82 (s, 3H), δ=3.36 (s, 3H), δ=2.45 (s, 3H); $^{13}$C-NMR (CDCl$_3$) δ=170.83, 168.81, 158.55, 156.70, 140.11, 139.63, 136.31, 135.14, 134.15, 131.75, 131.48, 130.69, 130.51, 129.80, 125.52, 119.10, 116.96, 115.73, 113.52, 112.40, 101.58, 56.28, 41.89, 27.17, 13.82; LRMS (FAB) 506.1 (M$^+$).

Example 27

Synthesis of 3-[1-(4-chlorobenzoyl)-5-methoxy-2-methyl-3-indolylmethyl]-1-(3,5-dichlorophenyl)-5-pyrazolone The title compound was obtained starting with the keto ester from Example 1 and 3,5-dichlorophenylhydrazine hydrochloride following the procedure described in Example 23. m.p. 104° to 105° C.; $^1$H-NMR (CDCl$_3$) δ=7.89 (s, 2H), δ=7.67 (d, 2H, J=8.49 Hz), δ=7.49 (d, 2H, J=8.49 Hz), δ=7.15 (bs,1H), δ=6.98 (bs, 1H), δ=6.81 (d, 1H, J=8.97 Hz), δ=6.67 (bd, 1H, J=9.03 Hz); $^{13}$C NMR (CDCl$_3$) δ=170.81, 168.81, 158.96, 156.71, 140.14, 136.36, 135.80, 134.11, 1131.75, 131.43, 130.63, 129.81, 125.24, 116.98, 115.76, 113.31, 112.42, 101.56, 56.26, 41.89, 27.14, 13.81; LRMS (FAB) 541 (M$^+$); Rf 0.64 (silica gel, EtOAc/hexanes 1:1).

Example 28

3-[1-(4-chlorobenzoyl)-5-methoxy-2-methyl-3-indolylmethyl]-1-(3-bromophenyl)-5-pyrazolone The title compound was obtained starting with the keto ester from Example 1 and 3-bromophenylhydrazine hydrochloride following the procedure described in Example 23. m.p. 164.5° to 167° C.; $^1$H-NMR (CDCl3) δ=8.09 (s, 1H), δ=7.89 (d, 1H, J=6.7Hz), δ=7.67 (d, 2H, J=4.6 Hz), δ=7.49 (d ,2H, J=4.6 HZ), δ=7.26–7.30 (m, 2H), δ=6.99 (s, 1H), δ=6.81 (d, 1H, J=9.1 Hz), δ=6.70 (d, 1H, J=2.5 HZ), δ=3.89 (s, 2H), δ=3.83 (s, 3H), δ=3.37 (s, 2H), δ=2.46 (s, 3H); HRMS: Moniosotopic Mass 550.05

Example 29

Synthesis of 3-[1-(4-chlorobenzoyl)-5-methoxy-2-methyl-3-indolylmethyl]-1-(3,5-dimethylphenyl)-5-pyrazolone The title compound was obtained starting with the keto ester from Example 1 and 3,5-dimethylphenylhydrazine hydrochloride following the procedure described in Example 23. m.p. 77.5° to 79.0° C.; $^1$H-NMR (CDCl3) δ=7.68–7.66 (d, 2H, J=8.6Hz), δ=7.48–7.50 (d, 3H, J=5.1 Hz), δ=7.26 (s, 1H), δ=7.00 (s, 1H), δ=6.81–6.84 (d, 2H, J=7.0 Hz), δ=6.67–6.70 (m, 1H) δ=3.89 (s, 2H), δ=3.82 (s, 3H), δ=3.33 (s, 2H), δ=2.50 (s, 3H), δ=2.34 (s, 6H); $^{13}$C-NMR (CDCl3) δ=170.84, 168.83, 157.99, 157.99, 156.68, 140.07, 139.15, 138.39, 136.21, 134.20, 121.75, 131.43, 130.77, 129.78, 127.58, 117.36, 115.71, 113.83, 112.46, 101.62, 41.83, 22.10, 22.06; Rf 0.20 (silica gel, 1:3 EtOAc/hexanes)

Example 30

Synthesis of 3-[1-(4-chlorobenzoyl)-5-methoxy-2-methyl-3-indolylmethyl]- 1-(3-nitrophenyl)-5-pyrazolone The title compound was obtained starting with the keto ester from Example 1 and 3-nitrophenylhydrazine hydrochloride following the procedure described in Example 23. m.p. 95° to 97° C.; $^1$H-NMR (CDCl$_3$) δ=8.72 (s, 1H), δ=8.33 (d,1H, J=8.25 Hz), δ=8.01 (d, 1H, J=8.25 Hz), δ=7.66 (bd, 2H), δ=7.48 (m, 4H), δ=7.31 (m, 1H), δ=6.99 (bs, 1H), δ=6.80 (d, 1H, J=9.06 Hz), δ=6.66 (bd, 1H, J=9.00 Hz), δ=3.91 (s, 2H), δ=3.81 (s, 3H), δ=3.42 (s, 3H); $^{13}$C-NMR (CDCl$_3$) δ=170.95, 168.55, 159.17, 156.72, 149.13, 140.18, 139.54, 136.41, 134.08, 131.77, 131.42, 130.63, 130.28, 129.82, 124.20, 119.90, 118.50, 115.76, 114.24, 113.74, 113.29, 112.41, 106.61, 101.52, 56.29, 41.92, 27.18, 13.83; LRMS (FAB) 517.2 (M+H$^+$); Rf 0.35 (silica gel, EtOAc/hexanes 1:1).

Example 31

Synthesis of 3-[1-(4-chlorobenzoyl)-5-methoxy-2-methyl-3-indolylmethyl]- 1-(3-methylphenyl)-5-pyrazolone The title compound was obtained starting with the keto ester from Example 1 and 3-methylphenylhydrazine hydrochloride following the procedure described in Example 23. m.p. 120° to 122° C.; $^1$H-NMR (CDCl$_3$) δ=7.68 (d, 2H, J=2.20 Hz), δ=7.66 (d, 2H, J=8.36 Hz), δ=7.48 (d, 2H, J=8.37 Hz), δ=7.28 (dt, 1 H, J=7.81 Hz), δ=7.02 (d, 1H, J=2.48 Hz), δ=7.01 (d, 1H, J=2.19 Hz), δ=6.85 (d, 1H, J=8.97 Hz), δ=6.69 (d, 1H, J$_{ab}$=2.38 Hz, J$_{ac}$=8.97 Hz), δ=3.88 (s, 2H), δ=3.82 (s, 3H), δ=3.33 (s, 2H), δ=2.45 (s, 3H), δ=2.39 (s, 3H); MS(LRFAB) 486.1 (M$^+$); Rf 0.41 (silica gel, EtOAc/hexanes 3:7).

Example 32

Synthesis of 3-[1-(4-chlorobenzoyl)-5-methoxy-2-methyl-3-indolylmethyl]- 1-(3-fluorophenyl)-5-pyrazolone The title compound was obtained starting with the keto ester from Example 1 and 3-fluorophenylhydrazine hydrochloride following the procedure described in Example 23. m.p. 162° to 164° C.; $^1$H-NMR (CDCl$_3$) δ=7.74 (1H, J=9.22 Hz), δ=7.70 (d, 1H, J=5.32 Hz), δ=7.68 (d, 2H, J=11.05 Hz), δ=7.49 (d, 2H, J=8.43 Hz), δ=7.35 (dt, 1H, J=8.12 Hz), δ=6.99 (d, 1H, J=2.51 Hz), δ=6.90 (dd, 1H, J$_{ab}$=2.19 Hz, J$_{ac}$=8.24 Hz), δ=6.84 (d, 1H, J=9.04 Hz), δ=6.69 (dd, 1H, J$_{ab}$=2.38, J$_{ac}$=9.03 Hz), δ=3.90 (s, 2H), δ=3.82 (s, 3H), δ=3.38 (s, 2H), δ=2.46 (s, 3H), $^{13}$C-NMR (CDCl$_3$) δ=170.87, 168.82, 158.54, 156.70, 140.07, 139.92, 136.32, 134.18, 131.75, 131.45, 130.77, 130.73, 130.65, 129.79, 115.74, 114.38, 114.34, 113.57, 112.34, 112.06, 106.64, 106.28, 101.64, 56.26, 41.95, 27.13, 13.83; LRMS (FAB) 490.1 (M+H$^+$); Rf 0.69 (silica gel, EtOAc/hexanes 1:1).

Example 33

Synthesis of 3-[1-(4-chlorobenzoyl)-5-methoxy-2-methyl-3-indolylmethyl]- 1-(3,4-dichlorophenyl)-5-pyrazolone The title compound was obtained starting with the keto ester from Example 1 and 3,4-dichlorophenylhydrazine hydrochloride following the procedure described in Example 23. m.p. 123° to 125° C.; $^1$H-NMR (CDCl$_3$) δ=8.07 (d, 1H, J=2.51 Hz) δ=7.84 (dd, 1H, J$_{ab}$=2.51 Hz, J$_{ac}$=8.85 Hz), δ7.67 (d, 2H, J=8.48 Hz), δ=7.49 (d, 2H, J=8.49 Hz), δ=7.44 (d, 1H, J=8.85 Hz), δ=6.98 (d, 1H, J=2.50 Hz), δ=6.83 (d, 1H, J=9.03 Hz), δ=6.69 (dd, 1H, J$_{ab}$=2.50 Hz, J$_{ac}$=9.04 Hz), δ=3.89 (s, 2H), δ=3.82 (s, 3H), δ=3.38 (s, 2H), δ=2.46 (s, 3H); MS (LRFAB) 541.1 (M$^+$); Rf 0.70 (silica gel, EtOAc/hexanes 3:7).

Example 34

Synthesis of 3-[1-(4-chlorobenzoyl)-5-methoxy-2-methyl-3-indolylmethyl]- 1-(4-methylphenyl)-5-pyrazolone The title compound was obtained starting with the keto ester from Example 1 and 4-methylphenylhydrazine hydrochloride following the procedure described in Example 23. m.p. 131° to 133° C.; $^1$H-NMR (CDCl$_3$) δ=7.74 (d, 2H, J=8.55 Hz), δ=7.68 (d, 2H, J=8.60 Hz), δ=7.49 (d, 2H, J=8.49 Hz), δ=7.21 (d, 2H, J=8.24 Hz), δ=7.00 (d, 1H, J=2.45 Hz), δ=6.84 (d, 1H, J=8.97 Hz ), δ=6.69 (dd, 1H, J$_{ab}$=2.32 Hz, J$_{ac}$=8.91 Hz), δ=3.89 (s, 2H), δ=3.82 (s, 3H), δ=3.35 (s, 2H), δ= 2.46 (s, 3H), δ=2.36 (s, 3H); MS (LRFAB) 486.1 (M$^+$); Rf 0.29 (silica gel, EtOAc/hexanes, 3:7).

Example 35

Synthesis of 3-[1-(4-chlorobenzoyl)-5-methoxy-2-methyl-3-indolylmethyl]-1-(3-methyl-6-pyridazinyl)-5-pyrazolone The title compound was obtained starting with the keto ester from Example 1 and 3-methyl-6-pyridazinylhydrazine hydrochloride following the procedure described in Example 23. This compound exists predominantly as the enolic tautomer as shown in Formula II. m.p. 122° to 124° C.; $^1$H-NMR (CDCl$_3$) δ=8.07 (d, 1H, J=9.04 Hz), δ=7.67 (d, 2H, J=8.48 Hz), δ=7.53 (d, 1H, J=9.09 Hz), δ=7.48 (d, 2H, J=8.48 Hz), δ=7.02 (d, 1H, J=2.51 Hz), δ=6.88 (d, 1H, J=9.04 Hz), δ=6.66 (dd, 1H, J$_{ab}$=2.56 Hz, J$_{ac}$=9.03 Hz), δ=5.41 (s, 1H), δ=3.95 (s, 2H), δ=3.81 (s, 3H), δ=3.77 (d, 1H, 2.54 Hz), δ=2.72 (s, 3H), δ=2.43 (s, 3H); Rf 0.06 (silica gel, MeOH/dichloromethane 1:9).

Example 36

Synthesis of 3-[1-(4-chlorobenzoyl)-5-methoxy-2-methyl-3-indolylmethyl]- 1-(2-quinoxalinyl)-5-pyrazolone The title compound was obtained starting with the keto ester from Example 1 and 2-quinoxalinylhydrazine hydrochloride following the procedure described in Example 23. This compound exists predominantly as the enolic tautomer as shown in Formula II. m.p. 231° to 233° C.; $^1$H-NMR (CDCl$_3$) δ=11.90 (s, 1H), δ=9.64 (s, 1H), δ=8.13 (d, 1H, 8.12 Hz), δ=7.88 (d, 1H, 6.78 Hz), δ=7.80 (t, 1H, 6.96 Hz), δ=7.73 (t, 1H, 6.97 Hz), δ=7.68 (d, 2H, J=8.42 Hz), δ=7.48 (d, 2H, J=8.55 Hz), δ=7.08 (d, 1H, J=2.50 Hz), δ=6.88 (d, 1H, J=8.97 Hz), δ=6.68 (dd, 1H, $J_{ab}$=2.51, $J_{ac}$=8.98 Hz), δ=5.46 (s, 1H), δ=4.02 (s, 2H), δ=3.82 (s, 3H), δ=2.46 (s, 3H); Rf 0.47 (silica gel, EtOAc/hexanes 1:1).

Example 37

Synthesis of 3-[1-(4-chlorobenzoyl)-5-methoxy-2-methyl-3-indolylmethyl]- 1-(4-trifluoromethylphenyl)-5-pyrazolone The title compound was obtained starting with the keto ester from Example 1 and 4-trifluoromethylphenylhydrazine hydrochloride following the procedure described in Example 23. m.p. 180° to 182° C.; $^1$H-NMR (CDCl$_3$) δ=8.06 (d, 2H, J=8.67 Hz), δ=7.67 (d, 2H, J=7.93 Hz), δ=7.65 (d, 2H J=7.70 Hz), δ=7.49 (d, 2H, J=8.37 Hz), δ=6.99 (d, 1H, J=2.26 Hz), δ=6.83 (d, 1H, J=9.10 Hz), δ=6.69 (dd, 1H, $J_{ab}$=2.32 Hz, $J_{ac}$=9.03 Hz), δ=3.91 (s, 2H), δ=3.81 (s, 3H), δ=3.40 (s, 2H), δ=2.47 (s, 3H); $^{13}$C-NMR (CDCl$_3$) δ=171.06, 168.81, 158.86, 156.70, 140.15, 136.41, 134.13, 131.76, 131.46, 130.69, 129.81, 126.75, 126.70, 126.65, 118.62, 115.74, 113.43, 112.25, 101.68, 56.27, 56.24, 41.92, 27.19, 13.79; Rf 0.75 (silica gel, EtOAc/hexanes 1:1).

Example 38

Synthesis of ethyl 4-[1-(3,4-dichlorobenzoyl)-5-methoxy-2-methyl-3-indolyl]-3-oxobutyrate The title compound was prepared following the procedure of Example 1.

Example 39

Synthesis of 3-[1-(3,4-dichlorobenzoyl)-5-methoxy-2-methyl-3-indolylmethyl]- 1-cyclohexyl-5-pyrazolone The title compound was obtained starting with the keto ester from Example 38 and cyclohexylhydrazine hydrochloride following the procedure described in Example 23. m.p. 104° to 107° C.; $^1$H-NMR (CDCl$_3$) δ=7.82 (d, 1H, J=1.77 Hz), δ=7.58(d, 1H, J=8.24 Hz), δ=7.51 (dd, 1H, $J_{ab}$=1.84 Hz, $J_{ac}$=8.31 Hz), δ=6.93 (d, 1H, J=2.32 Hz), δ=6.85 (d, 1H, J=9.04 Hz), δ=6.69 (dd, 1H, $J_{ab}$=2.51 Hz, $J_{ac}$=9.01 Hz), δ=3.99 (quintet, 1H), δ=3.82 (s, 3H), δ=3.78 (s, 2 H), δ=3.09 (s, 2H), δ=2.40 (s, 3H); $^{13}$C-NMR (CDCl$_3$) δ=171.82, 171.69, 167.47, 156.78, 138.09, 135.78, 135.63, 134.07, 132.06, 131.45, 131.20, 130.96, 129.32, 115.60, 114.74, 112.65, 101.61, 60.95, 56.17, 56.15, 52.86, 40.78, 31.63, 27.26, 26.00, 25.79, 21.61, 14.76, 13.80, 13.78; Rf 0.56 (silica gel, EtOAc/hexanes 1:1).

Example 40

Synthesis of 3-[1-(4-chlorobenzoyl)-5-methoxy-2-methyl-3-indolylmethyl]- 1-(3-aminophenyl)-5-pyrazolone 3-[1-(4-Chlorobenzoyl)-5-methoxy-2-methyl-3-indolylmethyl)]-1-(3-nitrophenyl)- 5-pyrazolone from Example 30 (510 mg, 0.98 mmol) was dissolved in 10 mL of ethyl acetate/methanol (4:1) with a catalytic amount of 5% Pd on C. The reaction mixture was hydrogenated at room temperature under 25 psi for 2.5 hours. The catalyst was removed by filtration over celite to afford upon evaporation of the solvent under reduced pressure the title pyrazolone. m.p. 118° to 120° C.; $^1$H-NMR (CDCl$_3$) δ=7.69 (d, 2H, J=8.25 Hz), δ=7.50 (d, 2H, J=8.25 Hz), δ=7.30 (m, 2H), δ=7.17 (t, 1H, J=8.01 Hz), δ=6.99 (bs, 1H), δ=6.86 (bd, 1H, J=8.91 Hz), δ=6.70 (bd, 1H, J=6.48 Hz), δ=6.53 (d, 1H, J=7.59 Hz), δ=3.87 (s, 2H), δ=3.81 (s, 3H), δ=3.33 (s, 2H), δ=2.48 (s, 3H); Rf 0.1 (silica gel, EtOAc/hexanes 1:1).

Example 41

Synthesis of 3-[1-(4-chlorobenzoyl)-5-methoxy-2-methyl-3-indolylmethyl]- 1-(3-acetamidophenyl)-5-pyrazolone The pyrazolone from Example 40 (141 mg, 0.289 mmol) was dissolved in 5 mL of methanol and reacted with acetic anhydride (40 μL, 0.29 mmol) at room temperature for 30 minutes. After evaporation of the solvent under reduced pressure, the crude material was purified on silica gel eluting with ethyl acetate/hexanes 1:1 to afford the title product. m.p. 124° to 126° C.; $^1$H-NMR (CDCl$_3$) δ=7.93 (s, 1H), δ=7.69 (d, 2H, J =8.46 Hz), δ=7.62 (bd, 1H), δ=7.54 (bd, 1H), δ=7.50 (d, 2H, J=8.49 Hz), δ=7.35 (t, 1H, J=8.13 Hz), δ=6.99 (s, 1H), δ=6.85 (d, 1H, J=8.91 Hz), δ=6.69 (bd, 1H, J=8.97 Hz), δ=3.88 (s, 2H), δ=3.81 (s, 3H), δ=3.36 (s, 2H), δ=2.45 (s, 3H), δ=2.18 (s, 3H); LRMS (FAB) 529 (M+H$^+$).

Example 42

Synthesis of ethyl 4-[1-(4-chlorophenyl)-5-methoxy-2-methyl-3-indolyl]-2-methyl -3-oxobutyrate The keto ester from Example 1 (500 mg, 1.16 mmol) in 10 mL of dry dimethylformamide was reacted with 28 mg of sodium hydride with stirring for 10 minutes. The reaction was then cooled to −10° C. and 164 mg of CH$_3$I in 1 mL of dimethylformamide is slowly added to the reaction mixture. The reaction was stirred for 3 hours at room temperature and then poured into 100 mL of ice cold 1N HCl. The mixture was extracted with two aliquots of 100 mL ethyl acetate and the organic phase was dried over sodium sulfate. After concentration, the residue was chromatographed on Kieselgel-60. The product elutes using 25% EtOAc/hexane (Rf 0.5) and is obtained as an oil. $^1$H-NMR (CDCl$_3$) δ=7.66 (d, 2H, J=8.25 Hz), δ=7.50 (d, 2H, J=8.16 Hz), 6.88 (d, 2H, J=8.79 Hz), 6.67 (bd, 1H, J=8.91 Hz), δ=4.17 (q, 2H, J=7.14 Hz), δ=3.87 (s, 2H), δ=3.83 (s, 3H), δ=3.47 (q, 1H, J=6.8 Hz), δ=2.37 (s, 3H), δ=1.7 (d, 2H, J=6.8 Hz), δ=1.25 (t, 3H, J=7.14 Hz).

Example 43

Synthesis of
3-[1-(4-chlorobenzoyl)-5-methoxy-2-methyl-3-
indolylmethyl]-
1-cyclohexyl-4-methyl-5-pyrazolone The title compound was obtained starting with the keto ester from Example 42 and cyclohexylhydrazine hydrochloride following the procedure described in Example 23. $^1$H-NMR (CDCl$_3$) δ=7.67 (d, 2H, J=8.49 Hz), δ=7.49 (d, 2H, J=8.43 Hz), δ=6.93 (d, 1H, J=2.37 Hz), δ=6.84 (d, 1H, J=5.61 Hz), δ=6.69 (dd, 1H, J=2.43, 8.91 Hz), δ=4.05 (m, 1H), 3.81 (s, 3H), δ=3.78 (q, 1H, J=6.8 Hz), δ=3.09 (s, 2H), δ=2.40 (s, 3H), δ=1.9 (d, 3H, J=6.75 Hz), δ=1.83–1.45 (m, 10H); $^{13}$C-NMR (CDCl$_3$) δ=171.77, 168.65, 156.89, 156.34, 135.77, 133.56, 131.73, 130.63, 129.52, 115.38, 114.09, 112.07, 101.24, 56.05, 52.56, 40.81, 31.44, 27.40, 25.93, 25.74, 13.62; LRMS (FAB) 492.4 (M+H$^+$); Rf 0.30 (silica gel, EtOAc/hexanes 1:1).

Example 44

Synthesis of
3-[1-(4-chlorobenzoyl)-5-methoxy-2-methyl-3-
indolylmethyl]-
1-cyclohexyl-4,4-dimethyl-5-pyrazolone Pyrazolone from Example 9 (300 mg, 0.62 mmol) was dissolved in dry acetone (5 mL) to which was added anhydrous potassium carbonate (100 mg, 0.7 mmol) and CH$_3$I (500 mg, 3 mmol). The reaction was stirred at room temperature for 5 hours under nitrogen. The reaction was filtered and solvent removed under reduce pressure. The residue was chromatographed on silica gel. The title compound elutes with 25% EtOAc/hexane. $^1$H-NMR (CDCl$_3$) δ=7.67 (d, 2H, J=8.49 Hz), δ=7.49 (d, 2H, J=8.43 Hz), δ=6.93 (d, 1H, J=2.37 Hz), δ=6.84 (d, 1H, J=5.61 Hz), δ=6.69 (dd, 1H, J=2.43, 8.91 Hz), δ=4.05 (m, 1H), δ=3.81 (s, 3H), δ=3.78 (s, 2H), δ=2.40 (s, 3H), δ=1.9 (d, 6 H), δ=1.83–1.45 (m, 10H); $^{13}$C-NMR (CDCl$_3$) δ=171.77, 168.65, 156.89, 156.34, 135.77, 133.56, 131.73, 130.63, 129.52, 115.38, 114.09, 112.07, 101.24, 56.05, 52.56, 40.81, 31.44, 27.40, 25.93, 25.74, 13.62; LRMS (FAB) 506.4 (M+H$^+$); Rf 0.6 (EtOAc/hexanes 1:1).

Example 45

Synthesis of
3-[1-(4-chlorobenzoyl)-5-methoxy-2-methyl-3-
indolylmethyl]-
1-cyclohexyl-4-benzylidene-5-pyrazolone Pyrazolone from Example 9 (150 mg, 0.31 mmol) was diluted in 5 mL of pyridine in the presence of 2 drops of piperidine and benzaldehyde (32 μL, 0.31 mmol). The reaction mixture was stirred at room temperature for 5 hours. The solvents are evaporated under reduced pressure and the crude material is purified by column chromatography over silica gel eluting with ethyl acetate/hexanes 1:3. The desired material is isolated as a clear oil.

Example 46

Synthesis of
3-[1-(4-chlorobenzoyl)-5-methoxy-2-methyl-3-
indolylmethyl]- 1-methyl-5-pyrazolone The title compound was prepared with the keto ester of Example 1 and methylhydrazine hydrochloride following the procedures set forth above. m.p. 146° to 147° C. $^1$H-NMR (CDCl$_3$) δ=7.67 (d, 2H, J=7.93 Hz), δ=7.65 (d, 2H, J=7.70 Hz), δ=6.99 (d, 1H, J=2.26 Hz), δ=6.83 (d, 1H, J=9.10 Hz), δ=6.69 (dd, 1H, J$_{ab}$=2.32, J$_{ac}$=9.03 Hz), δ=3.85 (s, 3H), δ=3.81 (s, 2H), δ=3.40 (s, 3H), δ=3.1 (s, 2H), δ=2.47 (s, 3H); LRMS (FAB) 566 (M+H$^+$); Rf 0.6 (EtOAc/hexanes 1:1).

Example 47

Synthesis of
3-[1-(4-chlorobenzoyl)-5-methoxy-2-methyl-3-
indolylmethyl]-
1-(3,4-dimethylphenyl)-5-pyrazolone The title compound can be prepared from the keto ester of Example 1 and 3,4-dimethylphenylhydrazine hydrochloride following the procedures set forth above.

Example 48

Synthesis of ethyl 6-[3-indolyl]-3-oxyhexyloate

The title ketoester can be prepared from 4-(3-indole)butyric acid in the manner of Example 1.

Example 49

Synthesis of
3-[3-indolyl-n-propyl]-1-cyclohexyl-5-pyrazolone

The title compound can be prepared from the ketoester of Example 48 and cyclohexylhydrazine hydrochloride in the manner described above.

Example 50

Synthesis of ethyl
4-[1-(2-naphthoyl)-5-methoxy-2-methyl-3-indolyl]-3-
oxobutyrate The title oxobutyrate was prepared in the manner of Example 1. $^1$H-NMR (CDCl$_3$) δ=8.27 (s, 1H), δ=7.97 (m, 4H), δ=7.76 (d, 1H, J=8.49 Hz), δ=7.62 (m, 2H), δ=6.87 (m, 2H), δ=6.64 (d, 1H, J=8.97 Hz), δ=4.16 (q, 2H), δ=3.90 (s, 2H), δ=3.82 (s, 3H), δ=3.50 (s, 2H), δ=2.40 (s, 3H), δ=1.25 (t, 3H, J=7.14 Hz); $^{13}$C-NMR (CDCl$_3$) δ=200.65, 170.06, 167.70, 156.63, 137.15, 135.95, 133.09, 133.03, 131.84, 131.69, 130.92, 129.90, 129.31, 129.22, 128.52, 127.71, 126.04, 115.76, 112.42, 111.91, 101.40, 62.09, 56.27, 48.48, 39.81, 14.67, 13.96.

Example 51

Synthesis of
3-[1-(2-naphthoyl)-5-methoxy-2-methyl-3-
indolylmethyl)]-
1-(3-trifluoromethylphenyl)-5-pyrazolone The title compound was prepared from the oxobutyrate of Example 50 and 3-trifluoromethylphenylhydrazine hydrochloride in the manner described above. The compound was recovered as an oil. $^1$H-NMR (CDCl$_3$) δ=8.27 (s, 1H), δ=8.20 (bs, 2H), δ=7.97 (m, 3H), is =7.77 (d, 1H, J=8.49 Hz), δ=7.66–7.43 (m, 5H), δ=7.03 (d, 1H J=2.43 Hz), δ=6.86 (d, 1H, J=9.03 Hz), δ=6.64 (dd, 1H, J=2.58, 9.09 Hz), δ=3.94 (s, 2H), δ=3.80 (s, 3H), δ=3.43 (s, 2H), δ=2.50 (s, 3H); $^{13}$C-NMR (CDCl$_3$) δ=170.99, 170.04, 158.94, 156.59, 139.10, 136.52, 135.99, 133.03, 131.82, 130.59, 130.04, 129.37, 128.55, 127.78, 125.98, 121.99, 115.88, 113.19, 112.40, 101.39, 56.19, 45.09, 41.91, 27.25, 13.82. LRMS(FAB) 556.3 (M+H$^+$).

Example 52

Synthesis of ethyl 4-[1-(benzoyl)-5-methoxy-2-methyl-3-indolyl]-oxobutyrate

The title oxobutyrate was prepared in the manner of Example 1. m.p. 97.5° to 101° C. $^1$H-NMR (CDCl$_3$) δ=7.70 (d, 2H, J=8.40 Hz), δ=7.61 (d, 1H, J=7.50 Hz), δ=7.47 (dd, 2H, J=7.30, 7.80 Hz), δ=6.86 (d, 2H, J=8.70 Hz), δ=6.64 (m, 1H), δ=4.12 (q, 2H, J=7.20 Hz), δ=3.87 (s, 2H), δ=3.83 (s, 3H), δ=3.46 (s, 2H), δ=2.36 (s, 3H), δ =1.23 (t, 3H, J=7.10 Hz). LRMS(FAB) 391.2 (M+H$^+$).

Example 53

Synthesis of 3-[1-benzoyl-5-methoxy-2-methyl-3-indolylmethyl]-1-(3-trifluoromethylphenyl)-5-pyrazolone The title compound was prepared from the oxobutyrate of Example 52 and 3-trifluoromethylphenylhydrazine hydrochloride in the manner described above. m.p. 60° to 64.5° C. $^1$H-NMR (CDCl$_3$) δ=8.17 (bs, 2H), δ=7.42 (m, 7H), δ=7.00 (s, 1H), δ=6.82 (d, 1H, J=8.90 Hz), δ= 6.65 (bd, 1H, J=9.00 Hz), δ=3.91 (s, 2H), δ=3.80 (s, 3H), δ=3.40 (s, 2H), δ=2.45 (s, 3H). LRMS(FAB) 506.1 (M+H$^+$). Elemental Analysis: C=66.57%, N=8.38%, and H =4.32%.

Example 54

Synthesis of ethyl 4-[1-(4-cyanobenzoyl)-5-methoxy-2-methyl -3-indolyl]-oxobutyrate The title oxobutyrate was prepared in the manner of Example 1. $^1$H-NMR (CDCl$_3$) δ=7.81 (s, 4H), δ=6.88 (d, 1H, J=2.50 Hz), δ=6.69 (d, 1H, J=9.00 Hz), δ=6.65 (dd, 1H, J=2.46, 9.03 Hz), δ=4.17 (q, 2H, J=7.10 Hz), δ=3.88 (s, 2H), δ=3.82 (s, 3H), δ=3.49 (s, 2H), δ=2.35 (s, 3H), δ=1.26 (t, 3H, J=7.10 Hz). LRMS(FAB) 419.2 (M+H$^+$).

Example 55

Synthesis of 3-[1-(4-cyanobenzoyl)-5-methoxy-2-methyl-3-indolylmethyl]-1-(4-trifluoromethylphenyl)-5-pyrazolone The title compound was prepared from the oxobutyrate of Example 54 and 4-trifluoromethylphenylhydrazine hydrochloride in the manner described above. m.p. 92° to 94° C. $^1$H-NMR (CDCl$_3$) δ=8.07 (d, 2H, J=9.15 Hz), δ=7.82 (s, 3H), δ=7.66 (d, 2H, J=8.85 Hz), δ=7.26 (s, 4H), δ=6.99 (bs, 1H), δ=6.73 (m, 2H), δ=3.91 (s, 2H), δ=3.81 (s, 3H), δ=3.40 (s, 2H), δ=2.46 (s, 3H). LRMS(FAB) 53 1.2 (M+H$^+$). Elemental Analysis: C=65.36%, N=10.28%, and H=4.01%.

Example 56

Synthesis of ethyl 4-[1-(4-methoxybenzoyl)-5-methoxy-2-methyl-3-indolyl]-oxobutyrate The title oxobutyrate was prepared in the manner of Example 1. m.p. 79° to 81° C. $^1$H-NMR (CDCl$_3$) δ=7.71 (d, 2H, J=8.80 Hz), δ=6.96 (d, 2H, J=8.90 Hz), δ=6.88 (m, 2H), δ=6.69 (bd, 1H), δ=4.17 (q, 2H, J=7.10 Hz), δ=3.91 (s, 3H), δ=3.87 (s, 2H), δ=3.83 (s, 3H), δ=3.47 (s, 2H), δ=2.39 (s, 3H), δ=1.25 (t, 3H, J=7.10 Hz). LRMS(FAB) 424.1 (M+H$^+$). Elemental Analysis: C=67.83%, N=3.26%, and H=5.77%.

Example 57

Synthesis of 3-[1-(4-methoxybenzoyl)-5-methoxy-2-methyl-3-indolylmethyl]- 1-cyclohexyl-5-pyrazolone The title compound was prepared from the oxobutyrate of Example 56 and cyclohexylhydrazine hydrochloride in the manner described above. m.p. 88° to 90° C. $^1$H-NMR (CDCl$_3$) δ=7.70 (d, 2H, J=8.80 Hz), δ=7.25 (s, 1H), δ=6.90 (d, 2H, J=8.88 Hz), δ=6.90 (s, $^1$H), δ=6.85 (d, 1H, J=7.70 Hz), δ=6.72 (dd, 1H, J=2.45, 7.75 Hz), δ=4.05 (m, 1H), δ=3.90 (s, 3H), δ=3.81 (s, 3H), δ=3.78 (s, 2H), δ=3.12 (s, 2H), δ=2.41 (s, 3H), δ=1.61–1.88 (m, 6H), δ=1.20–1.42 (m, 4H). LRMS(FAB) 474.3 (M+H$^+$). Elemental Analysis: C=68.61%, N=8.29%, and H=6.19%.

Example 58

Synthesis of 3-[1-(4-methoxybenzoyl)-5-methoxy-2-methyl-3-indolylmethyl]-1-(3-trifluoromethylphenyl)-5-pyrazolone The title compound was prepared from the oxobutyrate of Example 56 and 3-trifluoromethylphenylhydrazine hydrochloride in the manner described above. m.p. 91° to 94° C. $^1$H-NMR (CDCl$_3$) δ=8.19 (bs, 2H), δ=7.72 (d, 2H, J=8.80 Hz), δ=7.40 (m, 2H), δ=6.98 (d, 2H, J=9.00 Hz), δ=6.88 (d, 2H, J=9.10 Hz), δ=6.60 (bd, 1H), δ=3.90 (s, 6H), δ=3.80 (s, 2H), δ=2.50 (s, 3H). LRMS(FAB) 536.2 (M+H$^+$). Elemental Analysis: C=65.40%, N=7.39%, and H=4.28%.

Example 59

Synthesis of ethyl 4-[1-butanoyl-5-methoxy-2-methyl-3-indolyl]-oxobutyrate

The title oxobutyrate was prepared in the manner of Example 1. m.p. 71° to 72.5° C. $^1$H-NMR (CDCl$_3$) δ=7.81 (d,1H, J=9.72 Hz), δ=6.88 (m, 2H), δ=4.17 (q, 2H, J=7.11 Hz), δ=3.85 (s, 5H), δ=3.43 (s, 2H), δ=2.98 (t, 2H, J=7.44 Hz), δ=2.57 (s, 3H), δ=1.83 (m, 2H), δ=1.48 (m, 2H), δ=1.24 (t, 3H, J=7.17 Hz), δ=0.98 (t, 3H, J=7.35 Hz).

Example 60

Synthesis of 3-[1-butanoyl-5-methoxy-2-methyl-3-indolylmethyl]-1-cyclohexyl-5-pyrazolone The title compound was prepared from the oxobutyrate of Example 59 and cyclohexylhydrazine hydrochloride in the manner described above, and isolated as the hydrochloride salt. $^1$H-NMR (CDCl$_3$) δ=7.79 (d, 1H, J=9.12 Hz), δ=6.94 (d, 1H, J=2.58 Hz), δ=6.89 (dd, 1H, J=2.46, 9.06 Hz), δ=4.05 (m, 1H), δ=3.84 (s, 3H), δ=3.77 (s, 2H), δ=3.05 (s, 2H), δ=2.97 (t, 2H, J=7.65 Hz), δ=2.60 (s, 3H), δ=1.85–1.73 (m, 9H), δ=1.50–1.23 (m, 5H), δ=0.98 (t, 3H, J=7.41 Hz).

Example 61

Synthesis of ethyl 4-[1-(4-chlorobenzoyl)-5-chloro-2-methyl-3-indolyl]-3-oxobutyrate The title oxobutyrate was prepared in the manner of Example 1. m.p. 151–153° C. $^1$H-NMR (CDCl$_3$) δ=7.69 (d, 2H, J=8.40 Hz), δ=7.51 (d, 2H, J=8.40 Hz), δ=7.39 (s, 1H), δ=7.02 (d, 1H, J=8.30 Hz), δ=6.90 (d, 1H, J=8.70 Hz), δ=4.19 (q, 2H, J=7.10 Hz), δ=3.89 (s, 2H), δ=3.50 (s, 2H) δ=2.35 (s, 3H) δ=1.28 (t, 3H, J=7.02 Hz).

Example 62

Synthesis of 3-[1-chlorobenzoyl-5-chloro-2-methyl-3-indolylmethyl]-1-cyclohexyl-5-pyrazolone The title compound was prepared from the oxobutyrate of Example 61 and cyclohexylhydrazine hydrochloride salt in the manner described above, and isloated as the hydrochloride salt. m.p. 121° C. $^1$H-NMR (DMSO) δ=7.66 (m, 4H), δ=7.11 (d, 1H), δ=7.05 (d, 1H), δ=5.20 (s, 1H), δ=4.05 (m, 1H), δ=3.90 (s, 2H), δ=2.27 (s, 3H), δ=1.9–1.1 (m, 10H); LRMS (FAB) 482 (M+H$^+$); elemental analysis: C 61.20%, N 7.61% and H 5.23%.

Example 63

Synthesis of 3-[1-(4-chlorobenzoyl)-5-chloro-2-methyl-3-indolylmethyl]-1-(3-trifluoromethylphenyl)-5-pyrazolone The title compound was prepared from the oxobutyrate of Example 61 and 3-trifluoromethylphenyl hydrazine hydrochloride salt in the manner described above. m.p. 81–83° C. $^1$H-NMR (CDCl$_3$) δ=8.15 (m, 2H), δ=7.69 (d, 2H, J=8.60 Hz), δ=7.50 (m, 2H), δ=7.27 (m, 3H), δ=7.04 (d, 1H, J=6.80 Hz), δ=6.87 (d, 1H, J=8.90 Hz), δ=3.91 (s, 2H), δ=3.41 (s, 2H), δ=2.47 (s, 3H); LRMS (FAB) 544 (M+H$^+$); elemental analysis: C 58.93%, N 6.95% and H 4.06%.

Example 64

Synthesis of ethyl 4-[1-(4-methoxybenzoyl)-5-chloro-2-methyl-3-indolyl]-3-oxobutyrate The title oxobutyrate was prepared in the manner of Example 1. $^1$H-NMR (CDCl$_3$) δ=7.69 (d, 2H, J=8.90 Hz), δ=7.38 (s, 1H), δ=6.99 (m, 4H), δ=4.19 (q, 2H, J=7.10 Hz), δ=3.91 (s, 3H), δ=3.88 (s, 2H), δ<3.46 (s, 2H), δ=2.37 (s, 3H), δ=1.27 (t, 3H, J=6.40 Hz).

Example 65

Synthesis of 3-[1-(4-methoxybenzoyl)-5-chloro-2-methyl-3-indolylmethyl]-1-cyclohexyl-5-pyrazolone The title compound was prepared from the oxobutyrate of Example 64 and cyclohexylhydrazine hydrochloride salt in the manner described above, and isolated as the hydrochloride. m.p. 124–130° C. $^1$H-NMR (CDCl$_3$) δ=7.83 (d, 2H, J=8.90 Hz), δ=7.25 (d, 2H, J=8.80 Hz), δ=5.40 (s, 1H), δ=4.20 (m, 1H), δ=4.00 (s, 3H), δ=2.46 (s, 3H), δ=1.7–2.0 (m, 6H), δ=1.2–1.5 (m, 4H); LRMS (FAB) 478.5 (M+H$^+$); elemental analysis: C 63.11%, N 7.55% and H 5.57%.

Table 1 below summarizes the 3-indolyl-5-pyrazolone compounds of formula I:

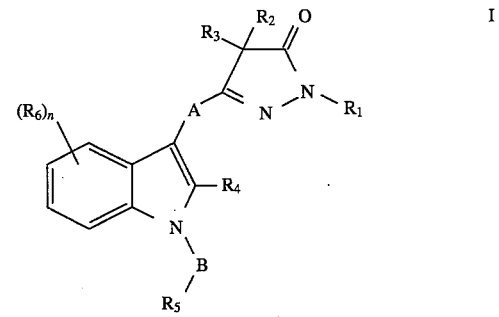

described above as well as additional such compounds prepared in the methods described above.

TABLE I

| R1 | R2 | R3 | R4 | R5 | R6 | A | B | Ex. No. |
|---|---|---|---|---|---|---|---|---|
| —CH$_3$ | H | H | —CH$_3$ | p-Cl-φ | —OCH$_3$ | —CH$_2$— | —C(O)— | 46 |
| 3,4-CH$_3$-φ | H | H | —CH$_3$ | p-Cl-φ | —OCH$_3$ | —CH$_2$— | —C(O)— | 47 |
| φ | H | H | —CH$_3$ | p-Cl-φ | —OCH$_3$ | —CH$_2$— | —C(O)— | 8 |
| cyclohexyl | H | H | —CH$_3$ | p-Cl-φ | —OCH$_3$ | —CH$_2$— | —C(O)— | 9 |
| cyclobutyl | H | H | —CH$_3$ | p-Cl-φ | —OCH$_3$ | —CH$_2$— | —C(O)— | 10 |
| cyclopentyl | H | H | —CH$_3$ | p-Cl-φ | —OCH$_3$ | —CH$_2$— | —C(O)— | 11 |
| cycloheptyl | H | H | —CH$_3$ | p-Cl-φ | —OCH$_3$ | —CH$_2$— | —C(O)— | 12 |
| benzyl | H | H | —CH$_3$ | p-Cl-φ | —OCH$_3$ | —CH$_2$— | —C(O)— | 13 |
| t-butyl | H | H | —CH$_3$ | p-Cl-φ | —OCH$_3$ | —CH$_2$— | —C(O)— | 14 |
| H | H | H | —CH$_3$ | p-Cl-φ | —OCH$_3$ | —CH$_2$— | —C(O)— | 15 |
| (n-C$_3$H$_7$)$_2$CH— | H | H | —CH$_3$ | p-Cl-φ | —OCH$_3$ | —CH$_2$— | —C(O)— | 16 |
| 4-CH$_3$O—C$_6$H$_4$— | H | H | —CH$_3$ | p-Cl-φ | —OCH$_3$ | —CH$_2$— | —C(O)— | 23 |
| 3-CH$_3$O—C$_6$H$_4$— | H | H | —CH$_3$ | p-Cl-φ | —OCH$_3$ | —CH$_2$— | —C(O)— | 24 |
| 3-CF$_3$—C$_6$H$_4$— | H | H | —CH$_3$ | p-Cl-φ | —OCH$_3$ | —CH$_2$— | —C(O)— | 25 |
| 3-Cl—C$_6$H$_4$— | H | H | —CH$_3$ | p-Cl-φ | —OCH$_3$ | —CH$_2$— | —C(O)— | 26 |
| 3,5-Cl—C$_6$H$_3$— | H | H | —CH$_3$ | p-Cl-φ | —OCH$_3$ | —CH$_2$— | —C(O)— | 27 |
| 3-Br—C$_6$H$_4$— | H | H | —CH$_3$ | p-Cl-φ | —OCH$_3$ | —CH$_2$— | —C(O)— | 28 |
| 3-NO$_2$—C$_6$H$_4$— | H | H | —CH$_3$ | p-Cl-φ | —OCH$_3$ | —CH$_2$— | —C(O)— | 30 |
| 4-CH$_3$—C$_6$H$_4$— | H | H | —CH$_3$ | p-Cl-φ | —OCH$_3$ | —CH$_2$— | —C(O)— | 34 |
| 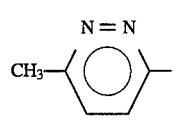 | H | H | —CH$_3$ | p-Cl-φ | —OCH$_3$ | —CH$_2$— | —C(O)— | 35 |

TABLE I-continued

| R1 | R2 | R3 | R4 | R5 | R6 | A | B | Ex. No. |
|---|---|---|---|---|---|---|---|---|
| 4-$CF_3$—$C_6H_4$— | H | H | —$CH_3$ | p-Cl-φ | —$OCH_3$ | —$CH_2$— | —C(O)— | 37 |
| 3-$NH_2$—$C_6H_4$— | H | H | —$CH_3$ | p-Cl-φ | —$OCH_3$ | —$CH_2$— | —C(O)— | 40 |
| 3-NHAc—$C_6H_4$— | H | H | —$CH_3$ | p-Cl-φ | —$OCH_3$ | —$CH_2$— | —C(O)— | 41 |
| cyclohexyl | H | —$CH_3$ | —$CH_3$ | p-Cl-φ | —$OCH_3$ | —$CH_2$— | —C(O)— | 43 |
| cyclohexyl | —$CH_3$ | —$CH_3$ | —$CH_3$ | p-Cl-φ | —$OCH_3$ | —$CH_2$— | —C(O)— | 44 |
| cyclohexyl | =CH-φ | — | —$CH_3$ | p-Cl-φ | —$OCH_3$ | —$CH_2$— | —C(O)— | 45 |
| cyclohexyl | H | H | —$CH_3$ | H | —$OCH_3$ | —$CH_2$— | BOND | 17 |
| cyclohexyl | H | H | H | p-Cl-φ | H | —$CH_2$— | —C(O)— | 19 |
| cyclohexyl | H | H | —$CH_3$ | -φ | —$OCH_3$ | —$CH_2$— | —$CH_2$— | 20 |
| cyclohexyl | H | H | —$CH_3$ | p-Cl-φ | —$OCH_3$ | —$CH_2CH_2$— | —C(O)— | 21 |
| cyclohexyl | H | H | —$CH_3$ | p-Cl-φ | H | —$CH_2$— | —C(O)— | 22 |
| cyclohexyl | H | H | —$CH_3$ | 3,4-Cl-φ | —$OCH_3$ | —$CH_2$— | —C(O)— | 39 |
| cyclohexyl | H | H | H | H | H | —$CH_2$— | BOND | 18 |
| cyclohexyl | H | H | H | H | H | —$CH_2CH_2CH_2$— | BOND | 49 |
| H | H | H | H | p-Cl-φ | H | —$CH_2$— | —C(O)— | A |
| 3-$CF_3$—$C_6H_4$— | H | H | —$CH_3$ | φ | —$OCH_3$ | —$CH_2$— | —C(O)— | 53 |
| 3-$CF_3$—$C_6H_4$— | H | H | —$CH_3$ | p-$C_3$HO-φ | —$OCH_3$ | —$CH_2$— | —C(O)— | 58 |
| 3-$CF_3$—$C_6H_4$— | H | H | —$CH_3$ | 2-$C_{10}H_{13}$ | —$OCH_3$ | —$CH_2$— | —C(O)— | 51 |
| 4-$CF_3$—$C_6H_4$— | H | H | —$CH_3$ | p-CN-φ | —$OCH_3$ | —$CH_2$— | —C(O)— | 55 |
| cyclohexyl | H | H | —$CH_3$ | φ | H | —$CH_2$— | —$CH_2$— | B |
| cyclohexyl | H | H | —$CH_3$ | φ | H | —$CH_2$— | BOND | C |
| cyclohexyl | H | H | H | H | H | —$CH_2CH_2$— | BOND | D |
| cyclohexyl | H | H | —$CH_3$ | p-$CH_3$O-φ | H | —$CH_2$— | —C(O)— | 57 |
| cyclohexyl | H | H | —$CH_3$ | iso-valeryl | —$OCH_3$ | —$CH_2$— | —C(O)— | 60 |
| quinoxalinyl (2-methylquinoxaline structure) | H | H | —$CH_3$ | p-Cl-φ | —$OCH_3$ | —$CH_2$— | —C(O)— | 36 |
| 3-$CH_3$—$C_6H_4$— | H | H | —$CH_3$ | p-Cl-φ | —$OCH_3$ | —$CH_2$— | —C(O)— | 31 |
| 3-F—$C_6H_4$ | H | H | —$CH_3$ | p-Cl-φ | —$OCH_3$ | —$CH_2$— | —C(O)— | 32 |
| 3,4-Cl—$C_6H_3$ | H | H | —$CH_3$ | p-Cl-φ | —$OCH_3$ | —$CH_2$— | —C(O)— | 33 |
| 3,5-$CH_3$—$C_6H_4$— | H | H | —$CH_3$ | p-Cl-φ | —$OCH_3$ | —$CH_2$— | —C(O)— | 29 |
| 2-$CH_3$—$C_6H_4$— | H | H | —$CH_3$ | p-Cl-φ | —$OCH_3$ | —$CH_2$— | —C(O)— | E |

Example 66

Ultraviolet Absorption Data

The ultraviolet (UV) absorption properties of two representative substituted 3-indolyl-5-pyrazolones were evaluated and compared to indomethacin [1-(4-chlorobenzoyl)-5-methoxy-2-methyl-$^1$H-indole-3-acetic acid], a compound known to absorb UV light (See page 4855 of the Merck Index, 10th Edition, Windholz, et al. Editor (1983)).

Specifically, 0.1 mg/mL of 3-indolyl-5-pyrazolone (Ex. 9 or 33) or indomethacin in methanol was added to a quartz cuvette (1 cm) and the UV absorption of this solution was then measured at a wavelength of from 200 nm to 800 nm (Examples 9 and 33) and from 190 nm to 800 nm. The results of this analysis are set forth in Table II below:

TABLE II

| Ex No. | λmax | Abs | $E^1$ | λother (shoulder) | range$^2$ |
|---|---|---|---|---|---|
| 9 | 251 nm | 2.3299 | 23.29 | 318 nm | 200 to ~350 nm |
| 33 | 254 nm | 2.3458 | 23.46 | 318 nm | 200 to ~350 nm |
| indomethacin | 246 nm | 2.3996 | 23.99 | 318 nm | 190 to ~350 nm |

$^1$E = Extinction coefficient (AU/mg/mL/cm)
$^2$range = range of UV absorption

These results illustrate that the substituted 3-indolyl-5-pyrazolones of this invention absorb UV radiation and, accordingly, are useful as additives for plastics or other materials where UV absorption is required.

Example 67

Cellular Screen for the Detection of Inhibitors of β-Amyloid Production

Numerous compounds of this invention were assayed for their ability to inhibit β-amyloid production in a cell line possessing the Swedish mutation. This screening assay employed cells (K293=human kidney cell line) which were stably transfected with the gene for amyloid precursor protein 751 (APP751) containing the double mutation $Lys_{651}Met_{652}$ to $Asn_{651}Leu_{652}$ (APP751 numbering) in the manner described in International Patent Application Publication No. 94/10569[1] and Citron et al.[16]. This mutation is commonly called the Swedish mutation and the cells, designated as "293 751 SWE", were plated in Corning 96-well plates at 1.5–2.5×10$^4$ cells per well in Dulbecco's minimal essential media plus 10% fetal bovine serum. Cell number is important in order to achieve β-amyloid ELISA results within the linear range of the assay (~0.2 to 2.5 ng per mL).

Following overnight incubation at 37° C. in an incubator equilibrated with 10% carbon dioxide, media were removed and replaced with 200 µL of a substituted 3-indolyl-5-pyrazolone (drug) containing media per well for a two hour pretreatment period and cells were incubated as above. Drag stocks were prepared in 100% dimethylsulfoxide such that at the final drug concentration used in the treatment, the concentration of dimethylsulfoxide did not exceed 0.5% and, in fact, usually equaled 0.1%.

At the end of the pretreatment period, the media were again removed and replaced with fresh drag containing media as above and cells were incubated for an additional two hours. After treatment, plates were centrifuged in a Beckman GPR at 1200 rpm for five minutes at room temperature to pellet cellular debris from the conditioned media. From each well, 100 µL of conditioned media or appropriate dilutions thereof were transferred into an ELISA plate precoated with antibody 266 against amino acids 13–28 of β-amyloid peptide as described in International Patent Application Publication No. 94/10569[1] and stored at 4° C. overnight. An ELISA assay employing labelled antibody 6C6 against amino acids 1–16 of β-amyloid peptide was run the next day to measure the amount of β-amyloid peptide produced.

Cytotoxic effects of the compounds were measured by a modification of the method of Hansen, et al.[17]. To the cells remaining in the tissue culture plate was added 25 µL of a 3,(4,5-dimethylthiazol-2-yl) 2,5-diphenyltetrazolium bromide (MTT) stock solution (5 mg/mL) to a final concentration of 1 mg/mL. Cells were incubated at 37° C. for one hour, and cellular activity was stopped by the addition of an equal volume of MTT lysis buffer (20% w/v sodium dodecylsulfate in 50% dimethylformamide, pH 4.7). Complete extraction was achieved by overnight shaking at room temperature. The difference in the $OD_{562nm}$ and the $OD_{650nm}$ was measured in a Molecular Device's $UV_{max}$ microplate reader as an indicator of the cellular viability.

The results of the β-amyloid peptide ELISA were fit to a standard curve and expressed as ng/mL β-amyloid peptide. In order to normalize for cytotoxicity, these results were divided by the MTT results and expressed as a percentage of the results from a 3-indolyl-5-pyrazalone free control. All results are the mean and standard deviation of at least six replicate assays.

The test compounds were assayed for β-amyloid peptide production inhibition activity in cells using this assay. The results of this assay demonstrate that, among others, the compounds of Examples 8, 9, 11, 12, 13, 14, 16, 17, 19, 20, 21, 22, 23, 24, 25, 26, 27, 29, 30, 31, 32, 33, 34, 37, 39, 43, 44, 46, 49, 51, 53, 55, 57, 58, 60, 62 and 63 each reduced β-amyloid peptide production by at least 20% as compared to control. Moreover, these compounds did not have a significant cytotoxic effect on the 293 751 SWE cells.

The results of this assay also demonstrated that the compounds of

Examples 15, 28, 40, 41, and 45 did not reduce β-amyloid peptide production by at least 20% as compared to control.

Thus, some of the compounds of this invention are useful in vitro in reducing β-amyloid peptide production and, accordingly, would be useful in vivo in treating AD.

Example 68

Cellular Screen for the Determining Toxicity of β-Amyloid Peptide to Neuronal Cells in the Presence of a 3-Indolyl-5-Pyrazolone Compound The purpose of this test is to determine the effect of 3-indolyl-5-pyrazolone compounds on the toxicity of β-amyloid peptide to neuronal cells.

Primary Rat Cortical Cell Cultures

Primary rat cortical cultures were established from 18 day rat fetuses. Cortical tissue was dissociated by incubation in a trypsin/EDTA solution (0.05% trypsin+0.53 mM EDTA in HBSS; GIBCO Laboratories, Grand Island, N.Y., USA) for 20 minutes at 37° C. The trypsin was then inactivated by resuspending the cells in serum-containing medium (DMEM/FBS): Dulbecco's Modified Eagles' Medium (DMEM) containing 4.5 g/L glucose, 1 mM sodium pyruvate, 1 mM glutamine, 100 Units/mL penicillin, 100 µg/mL streptomycin, and supplemented with 10% heat-inactivated fetal bovine serum (GIBCO Laboratories, Grand Island, N.Y., USA). Cells were then pelleted by centrifugation and resuspended in a chemically-defined medium (DMEM/B27: DMEM containing B27 supplement; GIBCO Laboratories, Grand Island, N.Y., USA) in place of FBS. Polyethyleneimine (PEI; Sigma Chemical Company, St. Louis, Mo., USA)-coated 6.4 mm (96-well) dishes were timed once with DMEM/FBS, and then seeded at 0.75 to 1.25×10⁵ cells per well in 0.1 mL DMEM/B27. Cultures were maintained in a $H_2O$-saturated incubator with an atmosphere of 90% air/ 10% $CO_2$ at 37° C. Cell viability was visually assessed by phase contrast microscopy and quantified by measuring the reduction of alamarBlue™ (Alamar biosciences, Inc., Sacramento, Calif., USA) as described below. Serum replacement with B27 supplement yields nearly pure neuronal cultures as judged by immunocytochemistry for glial fibrillary acidic protein and neuron-specific enolase (Brewer, et al.[20])

Primary Human Cortical Cell Culture

Primary human cortical cultures were prepared using a modification of the procedure described by Seubert, et al.[21] Following filtration through Nitex nylon screens, cortical tissue was resuspended in a trypsin/EDTA solution (0.05% trypsin+0.53 mM EDTA in HBSS; GIBCO Laboratories, Grand Island, N.Y., USA) and kept at 37° C. for 20 minutes. The trypsin was then inactivated by resuspending the cells in serum-containing medium (MEM/FBS: Modified Eagles' Medium (MEM) containing 1% glucose, 1 mM sodium pyruvate, 1 mM glutamine, and supplemented with 10% fetal bovine serum (GIBCO). Cells were then pelleted by centrifugation and resuspended in a chemically-defined medium (MEM/B27: MEM containing B27 supplement in place of FBS; GIBCO). Polyethyleneimine (PEI; Sigma Chemical Company, St. Louis, Mo., USA)-coated 6.4 mm (96-well) dishes were rinsed once with MEM/FBS, and then seeded at 0.75 to 1.25×10⁵ cells per well in 0.1 mL MEM/ B27. Cultures were maintained in a $H_2O$-saturated incubator with an atmosphere of 95% air/5% $CO_2$ at 37° C. The culture medium was exchanged twice weekly. Cell viability was visually assessed by phase contrast microscopy and quantified by measuring the reduction of alamarBlue™ (Alamar Biosciences, Inc., Sacramento, Calif., USA).

Experimental Treatments and Analysis of Neuronal Survival

β-amyloid peptide stock solutions were prepared as 1 mM stocks in sterile, doubly distilled water immediately prior to addition to cultures. Rat cortical neurons were exposed to β-amyloid peptide by removing the culture medium and replacing it with DMEM/$N_2$ (GIBCO Laboratories, Grand Island, N.Y., USA) containing 10 to 20 µM β-amyloid peptide. Human cortical neurons were exposed to test compound plus β-amyloid peptide by removing the culture medium and replacing it with MEM containing 50 µM β-amyloid peptide. Cultures were maintained for 2–3 days before neuronal survival was quantified using alamarBlue™.

Neurotoxicity Assay Using alamarBlue™

The alamarBlue™ assay incorporates a fluorometric/ colorimetric metabolic indicator (Alamar Biosciences, Inc. Sacramento, Calif., USA). Viable cells convert alamarBlue™ from an oxidized (non-fluorescent, blue) form to a reduced (fluorescent, red) form. Assays were preformed by replacing the culture media with a 10% alamarBlue™ solution in DMEM (rat cortical cultures) or MEM (human cortical cultures). Reduction of alamarBlue™ was determined spectrofluorometrically using a Millipore Cytofluor 2350 Scanner (excitation, 560 nm, emission, 590 nm) and CytoCalc™ software (Millipore Corp.) neuronal viability as assessed by alamarBlue™ was comparable to that obtained by measuring the fluorogenic probe Calcein AM, the release of the cytoplasmic enzyme lactate dehydrogenase (LDH), or the reduction of the tetrazolium salt, 2,3-bis(2-methoxy-4-nitro-5-sulfophenyl)- 2H-tetrazolium-5-carboxanilide (XTT; Diagnositic Chemistry LTD).

The results of the above described assay for human neuronal survival demonstrate that the compounds of Examples 8, 10, 15, 18, 19, 23, 24, 25, 26, 27, 30, 31, 32, 33, 34, 40, A, D and E inhibited by at least 25% (on average where more than one duplicate experiment was conducted) the toxicity of β-amyloid peptide to such cells. These results further indicate that the compound of Example 45 did not inhibit the toxicity of β-amyloid peptide to human neuronal cells at such a level.

The results of the above described assay for rat neuronal survival also demonstrate that the compounds of Examples 24, 25, 26, 27, 33, 34, A and E inhibited by at least 10% (on average where more than one duplicate experiment was conducted) the toxicity of β-amyloid peptide to such cells. These results further indicate that the compounds of Examples 8, 15, 18, 23, 30 and D did not inhibit the toxicity of rat neuronal cells at such a level.

Thus, some of the compounds of this invention are useful in vitro in inhibiting toxicity of β-amyloid peptide to neuronal cells and, in particular, human neuronal cells and, accordingly, would be useful in vivo in treating AD.

Example 69

5-Lipoxygenase Inhibition Data

5-Lipoxygenase catalyzes the oxidative metabolism of arachidonic acid to 5-hydroperoxyeicosatetraenoid acid (5-HETE), the initial reaction leading to the formation of the leukotrienes[18]. Accordingly, compounds inhibiting 5-lipoxygenase activity are art recognized to have anti-inflammatory properties.

The ability of test compounds to inhibit 5-lipoxygenase activity was determined in assays[19] using crude 5-lipoxygenase enzyme from rat basophilic leukemia cells (RBL-1). Test compounds are pre-incubated with the enzyme for 5 minutes at room temperature and the reaction is initiated by addition of substrate (arachidonic acid). Following an 8 minute incubation at room temperature, the reaction is terminated by addition of citric acid, and levels of 5-HETE determined by 5-HETE radioimmunoassay. The percent inhibition for 3 representative compounds of this invention are set forth in Table III below:

TABLE III

| Compound of Example No. | Concentration of Compound in assay | Percent Inhibition |
| --- | --- | --- |
| 9 | 6 μM | 75% |
| 14 | 7.5 μM | 48% |
| 25 | 6 μM | 60% |

The results of this example demonstrate that the compounds of this invention are inhibitors of 5-lipoxygenase and, accordingly, possess anti-inflammatory properties.

What is claimed is:

1. A compound of formula I:

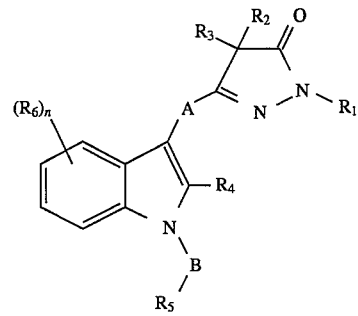

wherein $R_1$ is selected from the group consisting of hydrogen, alkyl of from 1 to 10 carbon atoms optionally substituted with 1 to 4 substituents selected from the group consisting of halo, —$NR_7R_8$, —$NR_7C(O)R_8$ where $R_7$ and $R_8$ are independently selected from the group consisting of hydrogen and alkyl of from 1 to 10 carbon atoms, aryl of from 6 to 10 carbon atoms, aryl of from 6 to 10 carbon atoms substituted with from 1 to 3 substituents selected from the group consisting of halo, cyano, nitro, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms, cycloalkyl of from 3 to 8 carbon atoms, aryl of from 6 to 10 carbon atoms optionally substituted with from 1 to 3 substituents selected from the group consisting of halo, nitro, cyano, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms, and heterocycles having from 2 to 8 carbon atoms and from 1 to 3 heteroatoms selected from the group consisting of oxygen, sulfur and nitrogen;

$R_2$ and $R_3$ are independently selected from the group consisting of hydrogen, alkyl of from 1 to 10 carbon atoms, and where $R_2$ and $R_3$ together define a substituent of the formula =$CR_{13}R_{14}$ where $R_{13}$ and $R_{14}$ are independently selected from the group consisting of hydrogen, alkyl of from 1 to 10 carbon atoms and phenyl;

$R_4$ is selected from the group consisting of hydrogen and alkyl of from 1 to 10 carbon atoms;

$R_5$ is selected from the group consisting of hydrogen, alkyl of from 1 to 10 carbon atoms optionally substituted with from 1 to 4 substituents selected from the group consisting of halo, —$NR_7R_8$, —$NR_7C(O)R_8$ where $R_7$ and $R_8$ are independently selected from the group consisting of hydrogen and alkyl of from 1 to 10 carbon atoms, aryl of from 6 to 10 carbon atoms optionally substituted with from 1 to 3 substituents selected from the group consisting of halo, nitro, cyano, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms, each $R_6$ is independently selected from the group consisting of halo, nitro, cyano, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms;

n is an integer of from 0 to 3;

A is selected from the group consisting of X—$R_9$— where X is selected from the group consisting of a bond, O and $S(O)_p$ where p is an integer of from 0 to 2 and $R_9$ is an alkylene group of from 1 to 6 carbon atoms; and B is selected from the group consisting of a bond, an alkylene group of from 1 to 6 carbon atoms, —$R_{10}$—Y— where $R_{10}$ is selected from the group consisting of a bond and an alkylene group of 1 to 4 carbon atoms and Y is selected from the group consisting of —C(O)— and —$S(O)_q$— where q is an integer of from 0 to 2, and —C(O)Z— where Z is selected from the group consisting of O, S, and —$NR_{11}$ where $R_{11}$ is hydrogen or alkyl of from 1 to 10 carbon atoms;

with the proviso that when $R_2$ and/or $R_3$ is hydrogen, the compounds of formula I above can exist in the tautomeric form illustrated in formula II below:

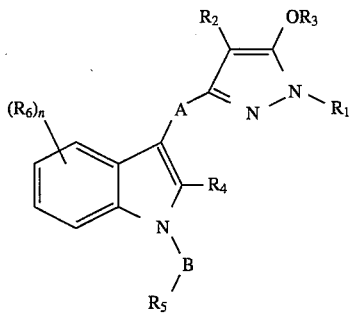

2. A compound according to claim 1 wherein $R_2$ and $R_3$ are hydrogen.

3. A compound according to claim 1 wherein $R_1$ is selected from the group consisting of alkyl of from 1 to 10 carbon atoms, aryl of from 6 to 10 carbon atoms optionally having from 1 to 2 substituents selected from the group consisting of fluoro, chloro, bromo, nitro, alkyl of from 1 to 3 carbon atoms, trihalomethyl, alkoxy of from 1 to 3 carbon atoms, —$NR_7R_8$, —$NR_7C(O)R_8$ where $R_7$ and $R_8$ are independently selected from the group consisting of hydrogen and alkyl of from 1 to 3 carbon atoms.

4. A compound according to claim 1 wherein $R_4$ is selected from the group consisting of hydrogen and methyl.

5. A compound according to claim 1 wherein $R_5$ is selected from the group consisting of aryl of from 6 to 10 carbon atoms optionally substituted with from 1 to 4 substituents selected from the group consisting of halo, nitro, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms.

6. A compound according to claim 5 wherein $R_5$ is selected from the group consisting of phenyl optionally substituted with 1 to 2 substituents selected from the group consisting of halo, nitro, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms.

7. A compound according to claim 6 wherein B is selected from the group consisting of a bond, and alkylene group of from 1 to 4 carbon atoms or —C(O)—.

8. A compound according to claim 1 wherein $R_6$ is selected from the group consisting of alkyl of from 1 to 10 carbon atoms and alkoxy of from 1 to 10 carbon atoms and n is an integer equal to 1.

9. A compound according to claim 8 wherein $R_6$ is at the 5-position of the indole ting and is an alkoxy group of from 1 to 4 carbon atoms.

10. A compound according to claim 1 which compound is selected from the group consisting of:

3-[1-(4-chlorobenzoyl)-5-methoxy-2-methyl-3-indolylmethyl]-1-phenyl-5-pyrazolone 3-[1-(4-chlorobenzoyl)-5-methoxy-2-methyl-3-indolylmethyl]-1-cyclohexyl-5-pyrazolone 3-[1-(4-chlorobenzoyl)-5-methoxy-2-methyl-3-indolylmethyl]-1-cyclobutyl-5-pyrazolone 3-[1-(4-chlorobenzoyl)-5-methoxy-2-methyl-3-indolylmethyl]-1-cyclopentyl-5-pyrazolone 3-[1-(4-chlorobenzoyl)-5-methoxy-2-methyl-3-indolylmethyl]-1-cycloheptyl-5-pyrazolone 3-[1-(4-chlorobenzoyl)-5-methoxy-2-methyl-3-indolylmethyl]-1-benzyl-5-pyrazolone 3-[1-(4-chlorobenzoyl)-5-methoxy-2-methyl-3-indolylmethyl]-1-t-butyl-5-pyrazolone 3-[1-(4-chlorobenzoyl)-5-methoxy-2-methyl-3-indolylmethyl]-5-pyrazolone 3-[1-(4-chlorobenzoyl)-5-methoxy-2-methyl-3-indolylmethyl]-1-(4-heptyl)- 5-pyrazolone 3-(5-methoxy-2-methyl-3-indolylmethyl)-1-cyclohexyl -5-pyrazolone 3-[1-(4-chlorobenzoyl)-3-indolylmethyl]-1-cyclohexyl-5-pyrazolone 3-(1-benzyl-5-methoxy-2-methyl-3-indolylmethyl)-1-cyclohexyl-5-pyrazolone 3-[1-(4-chlorobenzoyl)-5-methoxy-2-methyl-3-indolylethyl]-1-cyclohexyl-5-pyrazolone 3-[1-(4-chlorobenzoyl)-2-methyl-3-indolylmethyl]-1-cyclohexyl-5-pyrazolone 3-[1-(4-chlorobenzoyl)-5-methoxy-2-methyl-3-indolylmethyl]-1-(4-methoxyphenyl)- 5-pyrazolone 3-[1-(4-chlorobenzoyl)-5-methoxy-2-methyl-3-indolylmethyl]-1-(3-methoxyphenyl)- 5-pyrazolone 3-[1-(4-chlorobenzoyl)-5-methoxy-2-methyl-3-indolylmethyl]-1-( 3-trifluoromethylphenyl)-5-pyrazolone 3-[1-(4-chlorobenzoyl)-5-methoxy-2-methyl-3-indolylmethyl]-1-( 3-chlorophenyl)-5-pyrazolone 3-[1-(4-chlorobenzoyl)-5-methoxy-2-methyl-3-indolylmethyl]-1-( 3,5-dichlorophenyl)-5-pyrazolone 3-[1-(4-chlorobenzoyl)-5-methoxy-2-methyl-3-indolylmethyl]-1-( 3-bromophenyl)-5-pyrazolone 3-[1-(4-chlorobenzoyl)-5-methoxy-2-methyl-3-indolylmethyl]-1-( 3,5-dimethylphenyl)-5-pyrazolone 3-[1-(4-chlorobenzoyl)-5-methoxy-2-methyl-3-indolylmethyl]-1-( 3-nitrophenyl)-5-pyrazolone 3-[1-(4-chlorobenzoyl)-5-methoxy-2-methyl-3-indolylmethyl]-1-( 3-methylphenyl)-5-pyrazolone 3-[1-(4-chlorobenzoyl )-5-methoxy-2-methyl-3-indolylmethyl]-1-( 3-fluorophenyl)-5-pyrazolone 3-[1-(4-chlorobenzoyl)-5-methoxy-2-methyl-3-indolylmethyl]-1-( 3,4-dichlorophenyl)-5-pyrazolone 3-[1-(4-chlorobenzoyl)-5-methoxy-2-methyl-3-indolylmethyl]-1-( 4-methylphenyl)-5-pyrazolone 3-[1-(4-chlorobenzoyl)-5-methoxy-2-methyl-3-indolylmethyl]-1-( 3-methyl-6-pyridazinyl)-5-pyrazolone 3-[1-(4-chlorobenzoyl)-5-methoxy-2-methyl-3-indolylmethyl]-1-( 2-quinoxalinyl)-5-pyrazolone 3-[1-(4-chlorobenzoyl)-5-methoxy-2-methyl-3-indolylmethyl]-1-( 4-trifluoromethylphenyl)-5-pyrazolone 3-[1-(3,4-dichlorobenzoyl)-5-methoxy-2-methyl-3-indolylmethyl]-1-cyclohexyl- 5-pyrazolone 3-[1-(4-chlorobenzoyl)-5-methoxy-2-methyl-3-indolylmethyl]-1-( 3-aminophenyl)-5-pyrazolone 3-[1-(4-chlorobenzoyl)-5-methoxy-2-methyl-3-indolylmethyl]-1-( 3-acetamidophenyl)-5-pyrazolone
3-[1-(4-dichlorobenzoyl)-5-methoxy-2-methyl-3-indolylmethyl]-1-cyclohexyl- 4-methyl-5-pyrazolone
3-[1-(4-dichlorobenzoyl)-5-methoxy-2-methyl-3-indolylmethyl]-1-cyclohexyl- 4,4-dimethyl-5-pyrazolone
3-[1-(4-dichlorobenzoyl)-5-methoxy-2-methyl-3-indolylmethyl]-1-cyclohexyl- 4-benzylidene-5-pyrazolone
3-[1-(4-chlorobenzoyl)-5-methoxy-2-methyl-3-indolylmethyl]-1-methyl-5-pyrazolone
3-[1-(4-chlorobenzoyl)-5-methoxy-2-methyl-3-indolylmethyl]-1-( 3,4-dimethylphenyl )-5-pyrazolone
3-(3-indolylmethyl)-1-cyclohexyl-5-pyrazolone
3-(3-indolyl-n-propyl)-1-cyclohexyl-5-pyrazolone
3-[1-(4-chlorobenzoyl)-3-indolylmethyl]-5-pyrazolone
3-[1-(benzoyl)-5-methoxy-2-methyl-3-indolylmethyl]-1-( 3-trifluoromethyl)-5-pyrazolone
3-[1-(4-methoxybenzoyl)-5-methoxy-2-methyl-3-indolylmethyl]-1-( 3-trifluoromethyl)-5-pyrazolone
3-[1-(2-naphthoyl)-5-methoxy-2-methyl-3-indolylmethyl]-1-( 3-trifluoromethyl)-5-pyrazolone
3-[1-(4-cyanobenzoyl)-5-methoxy-2-methyl-3-indolylmethyl]-1-( 3-trifluoromethylphenyl)-5-pyrazolone
3-(1-benzyl-2-methyl-3-indolylmethyl)-1-cyclohexyl-5-pyrazolone
3-(1-phenyl-2-methyl-3-indolylmethyl)-1-cyclohexyl-5-pyrazolone
3-(3-indolylethyl)-1-cyclohexyl-5-pyrazolone
3-[1-(4-methoxybenzoyl)-5-methoxy-2-methyl-3-indolylmethyl]-1-cyclohexyl-5-pyrazolone
3-[1-(4-methoxybenzoyl)-5-methoxy-2-methyl-3-indolylmethyl]-1-( 4-trifluoromethylphenyl)-5-pyrazolone
3-[1-butoyl-5-methoxy-2-methyl-3-indolylmethyl]-1-cyclohexyl-5-pyrazolone.

11. A compound of formula IV below:

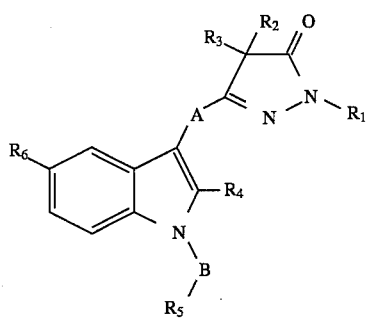

wherein $R_1$ is selected from the group consisting of hydrogen, alkyl of from 1 to 10 carbon atoms optionally substituted with 1 to 4 substituents selected from the group consisting of halo, aryl of from 6 to 10 carbon atoms optionally substituted with from 1 to 3 substituents selected from the group consisting of fluoro, chloro, nitro, cyano, alkyl of from 1 to 10 carbon atoms, haloalkyl of from 1 to 10 carbon atoms and at least 1 halo substituent, alkoxy of from 1 to 10 carbon atoms, cycloalkyl of from 3 to 8 carbon atoms, aryl of from 6 to 10 carbon atoms optionally substituted with from 1 to 3 substituents selected from the group consisting of fluoro, chloro, nitro, cyano, alkyl of from 1 to 10 carbon atoms, haloalkyl of from 1 to 10 carbon atoms and at least 1 halo substituent, alkoxy of from 1 to 10 carbon atoms, and $R_4$ is selected from the group consisting of hydrogen and alkyl of from 1 to 40 carbon atoms;

$R_5$ is selected from the group consisting of hydrogen, alkyl of from 1 to 10 carbon atoms optionally substituted with from 1 to 4 substituents selected from the group consisting of halo, —$NR_7R_8$, —$NR_7C(O)R_8$ where $R_7$ and $R_8$ are independently selected from the group consisting of hydrogen and alkyl of from 1 to 10 carbon atoms, aryl of from 6 to 10 carbon atoms optionally substituted with from 1 to 3 substituents selected from the group consisting of halo, nitro, cyano, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms, $R_6$ is selected from the group consisting of halo, nitro, amino, alkyl of from 1 to 10 carbon atoms, haloalkyl of from 1 to 10 carbon atoms and at least 1 halo substituent, alkoxy of from 1 to 10 carbon atoms, —$NR_7R_8$, —$NR_7C(O)R_8$ where $R_7$ and $R_8$ are independently selected from the group consisting of hydrogen and alkyl of from 1 to 10 carbon atoms;

A is selected from the group consisting of X—$R_9$— where X is selected from the group consisting of a bond, O and $S(O)_p$ where p is an integer of from 0 to 2 and $R_9$ is an alkylene group of from 1 to 6 carbon atoms; and B is selected from the group consisting of a bond, an alkylene group of from 1 to 6 carbon atoms, —$R_{10}$—Y— where $R_{10}$ is selected from the group consisting of a bond and an alkylene group of 1 to 4 carbon atoms and Y is selected from the group consisting of —C(O)— and —$S(O)_q$— where q is an integer of from 0 to 2, and —C(O)Z— where Z is selected from the group consisting of O, S, and —$NR_{11}$ where $R_{11}$ is hydrogen or alkyl of from 1 to 10 carbon atoms;

with the proviso that when $R_2$ and/or $R_3$ is hydrogen, the compounds of formula IV above can exist in the tautomeric form illustrated in formula V below:

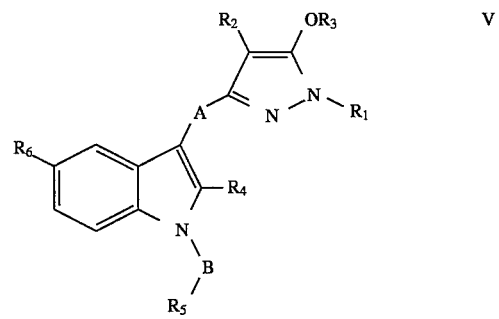

* * * * *